United States Patent [19]

Keenan et al.

[11] Patent Number: 5,741,804
[45] Date of Patent: Apr. 21, 1998

[54] SUBSTITUTED BENZIMAZOLES WHICH INHIBIT PLATELET AGGRECATION

[75] Inventors: Richard McCulloch Keenan, Malvern; William Henry Miller, Schwenksville, both of Pa.

[73] Assignee: SmithKline Beecham Corporation, Philadelphia, Pa.

[21] Appl. No.: 446,791

[22] PCT Filed: Dec. 1, 1993

[86] PCT No.: PCT/US93/11779

§ 371 Date: May 30, 1995

§ 102(e) Date: May 30, 1995

[87] PCT Pub. No.: WO94/12478

PCT Pub. Date: Jun. 9, 1995

[30] Foreign Application Priority Data

Dec. 1, 1992 [GB] United Kingdom ............... 9225141

[51] Int. Cl.$^6$ ............... C07D 235/12; A61K 31/415
[52] U.S. Cl. ............... 514/394; 546/199; 548/308.7; 548/310.1; 548/494; 514/388; 514/322; 514/419

[58] Field of Search ............... 548/308.7, 310.1; 514/388, 394

[56] References Cited

U.S. PATENT DOCUMENTS 4,634,783  1/1987  Fujii et al. ............... 549/475
5,272,167  12/1993  Girijavallabhan et al. ............... 514/394

*Primary Examiner*—Johann Richter
*Assistant Examiner*—Laura L. Stockton
*Attorney, Agent, or Firm*—Mary E. McCarthy; Stephen Venetianer; Edward T. Lentz

[57] ABSTRACT

This invention relates to compounds of the formula:

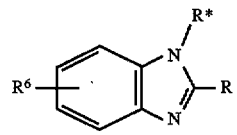

which are effective for inhibiting platelet aggregation, pharmaceutical compositions for effecting such activity, and a method for inhibiting platelet aggregation.

8 Claims, No Drawings

SUBSTITUTED BENZIMAZOLES WHICH INHIBIT PLATELET AGGRECATION

This application is a 371 of PCT/US93/11779 filed Dec. 1, 1993.

FIELD OF THE INVENTION

This invention relates to novel bicyclic compounds which inhibit platelet aggregation, pharmaceutical compositions containing the compounds and methods of using the compounds.

BACKGROUND OF THE INVENTION

Platelet aggregation is believed to be mediated primarily through the fibrinogen receptor, or GPIIb-IIIa platelet receptor complex, which is a member of a family of adhesion receptors referred to as integrins. It has been found that frequently the natural ligands of integrin receptors are proteins which contain an Arg—Gly—Asp sequence (RGD in single letter amino acid code). Von Willebrand factor and fibrinogen, which are considered to be natural ligands for the GPIIb-IIIa receptor, possess an RGD sequence in their primary structure. Functionally, these proteins are able to bind and crosslink GPIIb-IIIa receptors on adjacent platelets and thereby effect aggregation of platelets.

Fibronectin, vitronectin and thrombospondin are RGD-containing proteins which have also been demonstrated to bind to GPIIb-IIIa. Fibronectin is found in plasma and as a structural protein in the intracellular matrix. Binding between the structural proteins and GPIIb-IIIa may function to cause platelets to adhere to damaged vessel walls.

Linear and cyclic peptides which bind to vitronectin and contain an RGD sequence are disclosed in WO 89/05150 (PCT US88/04403). EP 0 275 748 discloses linear tetra- to hexapeptides and cyclic hexa- to octapeptides which bind to the GPIIb-IIIa receptor and inhibit platelet aggregation. Other linear and cyclic peptides, the disclosure of which are incorporated herein by reference, are reported in EP-A 0 341 915. However, the peptide like structures of such inhibitors often pose problems, such as in drug delivery, metabolic stability and selectivity. Inhibitors of the fibrinogen receptor which are not constructed of natural amino acid sequences are disclosed in EP-A 0 372A86, EP-A 0 381 033 and EP-A 0 478 363. WO 92/07568 (PCT/US91/08166) discloses fibrinogen receptor antagonism which mimic a conformational γ-turn in the RGD sequence by forming a monocyclic seven-membered ting structure. There remains a need, however, for novel fibrinogen receptor antagonists (e.g. inhibitors of the GPIIb-IIIa protein) which have potent in vivo and in vitro effects and lack the peptide backbone structure of amino acid sequences.

The present invention discloses novel bicyclic compounds, including benzimidazoles. These compounds inhibit binding to the GPIIb-IIIa receptor and inhibit platelet aggregation.

SUMMARY OF THE INVENTION

In one aspect this invention is a bicyclic compound comprising a substituted six-membered ring fused to a substituted five-membered ring as described hereinafter in formula (I).

This invention is also a pharmaceutical composition for inhibiting platelet aggregation or clot formation, which comprises a compound of formula (I) and a pharmaceutically acceptable carrier.

This invention is further a method for inhibiting platelet aggregation in a mammal in need thereof, which comprises internally administering an effective amount of a compound of formula (I).

In another aspect, this invention provides a method for inhibiting reocclusion of an artery or vein in a mammal following fibrinolytic therapy, which comprises internally administering an effective amount of a fibrinolytic agent and a compound of formula (I). This invention is also a method for treating stroke, transient ischemia attacks, myocardial infarction, or atherosclerosis.

DETAILED DESCRIPTION OF THE INVENTION

This invention discloses novel bicyclic compounds which inhibit platelet aggregation. The novel bicyclic compounds comprise a five-membered ring fused to an aromatic six membered ring and having a nitrogen-containing substituent on the six membered ring and an aliphatic substituent, preferably containing an acidic moiety, on the five membered ring. The five membered ring may contain heteroatoms, such as nitrogen, oxygen and sulfur, and the six membered ring may be carbocyclic or contain up to two nitrogen atoms. The fused 6-5 ring system is believed to interact favorably with the GPIIb-IIIa receptor and to orient the substituent sidechains on the six and five membered rings so that they may also interact favorably with the receptor.

Although not intending to be bound to any specific mechanism of action, these compounds are believed to inhibit the binding of fibrinogen to the platelet-bound fibrinogen receptor GPIIb-IIIa, and may interact with other adhesion proteins via antagonism of a putative RGD binding site.

The compounds of this invention are compounds of formula (I):

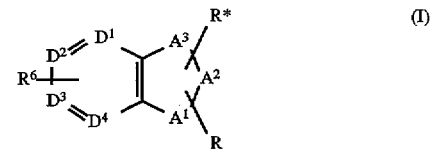

wherein:

$A^1$ to $A^3$ form any accessible substituted five-membered ring, which may be saturated or unsaturated, optionally containing up to two heteroatoms chosen from the group of O, S and N wherein S and N may be optionally oxidized;

$D^1$ to $D^4$ form any accessible substituted six membered ring, optionally containing up to two nitrogen atoms;

R is at least one substituent chosen from the group of $R^7$, or Q—$C_{1-4}$alkyl, Q—$C_{2-4}$alkenyl, Q—$C_{2-4}$alkynyl, Q—$C_{3-4}$oxoalkenyl or Q—$C_{3-4}$oxoalkynyl, Q—$C_{1-4}$aminoalkyl, Q—$C_{3-4}$aminoalkenyl, or Q—$C_{3-4}$aminoalkynyl, optionally substituted by any accessible combination of one or more of $R^{11}$ or $R^7$;

R* is absent or present as H, Q—$C_{1-6}$alkyl, Q—$C_{1-6}$alkyl, Q—$C_{1-6}$oxoalkyl, Q—$C_{2-7}$alkenyl, Q—$C_{3-4}$oxoalkenyl, Q—$C_{3-4}$oxoalkylnyl, Q—$C_{2-4}$alkynyl, $C_{3-6}$cycloalkyl, Ar, or Het, optionally substituted by one or more of $R^{11}$;

each Q independently is H, $C_{3-6}$cycloalkyl, Het or Ar;

$R^6$ is W—$(CR'_2)_q$—Z—$(Cr'R^{10})_r$—U—$(CR'_2)_s$—V—;

each $R^7$ independently is —$COR^8$, —$COCR'_2R^9$, —C(S)$R^8$, —S(O)$_m$OR', —S(O)$_m$NR'R", —PO(OR'), —PO(OR')$_2$, —B(OR')$_2$, —$NO_2$, or tetrazolyl;

each R⁸ independently is —OR', —NR'R", —NR'SO₂R',
—NR'OR', —OCR'₂CO(O)R', or AA;

R⁹ is —OR', —CN, —S(O)ᵣR', —S(O)ₘNR'₂, —C(O)R',
C(O)NR'₂, or —CO₂R';

R¹⁰ is H, $C_{1-4}$alkyl or —NR'R";

each R¹¹ independently is H, halo, —OR¹², —CN,
—NR'R¹², —NO₂, —CF₃, CF₃S(O)ᵣ—, —CO₂R',
—CONR'₂, Q—$C_{0-6}$alkyl—, Q—$C_{0-6}$alkylamino- or
Q—$C_{0-6}$alkyl-S(O)ᵣ—; Q—$C_{2-6}$alkynyl—,
Q—$C_{0-6}$alkyloxy—, Q—$C_{0-6}$alkylamino- or
Q—$C_{0-6}$alkyl-S(O)ᵣ—;

each R¹² independently is ', —C(O)R', —C(O)NR'₂,
—C(O)OR', —S(O)ₘR', or —S(O)ₘNR'₂;

each R' independently is H, $C_{1-4}$alkyl, $C_{3-7}$cycloalkyl-
$C_{0-4}$alkyl, or Ar—$C_{0-4}$alkyl;

each R" independently is R' or —C(O)R';

AA is an amino acid with the carboxyl group optionally protected;

U and V are absent or CO, CR'₂, C(=CR'₂), S(O)ₙ, O,
NR', CR'OR', CR'(OR")CR'₂, CR'₂CR'(OR"), C(O)
CR'₂, CR'₂C(O), CONR', NR'CO, OC(O), C(O)O, C(S)
O, OC(S), C(S)NR', NR'C(S), S(O)ₙNR', NR'S(O)ₙ,
N=N, NR'NR', NR'CR'₂, NR'CR'₂, CR'₂O, OCR'₂,
C≡C, or CR'=CR', provided that U and V are not simultaneously absent;

W is R'R"N—, R'R"NR'N—, R'R"NR'NCO—, R'₂NR'NC
(=NR')—,

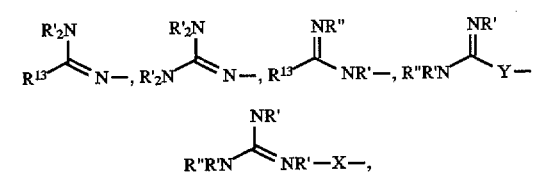

or Ⓔ;

X is absent, N=CR', C(O), or O;

Y is absent, S, or O;

Z is (CH₂)ᵣ, Het, Ar, or $C_{3-7}$cycloalkyl;

each m independently is 1 or 2;

each n independently is 0 to 3;

q is 0 to 3;

each r independently is 0 to 2;

each s independently is 0 to 2; and each t independently is 0 to 2;

or a pharmaceutically acceptable salt thereof.

Also included in this invention are complexes or prodrugs of the compounds of this invention. Prodrugs are considered to be any covalently bonded carriers which release the active parent drug according to formula (I) in vivo.

In cases wherein the compounds of this invention may have one or more chiral centers, unless specified, this invention includes each unique nonracemic compound which may be synthesized and resolved by conventional techniques. In cases in which compounds have unsaturated carbon-carbon double bonds, both the cis (Z) and trans (E) isomers are within the scope of this invention. In cases wherein compounds may exist in tautomeric forms, such as keto-enol tautomers, such as

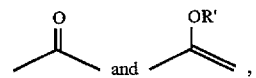

and tautomers of guanidine-type groups, such as

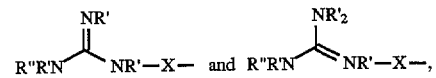

each tautomeric form is contemplated as being included within this invention whether existing in equilibrium or locked in one form by appropriate substitution with R'. The meaning of any substituent at any one occurrence is independent of its meaning, or any other substituent's meaning, at any other occurrence, unless specified otherwise.

With reference to formula (I), suitably,

A¹ is CR¹R¹', CR¹, NR¹, N, O, or S(O)ₓ;

A² is CR²R²', CR², or NR²;

A³ is CR³R³', CR³, NR³, N, O, or S(O)ₓ;

D¹–D⁴ and CR¹¹, CR⁶ or N;

R is (CR¹⁴R¹⁵)ᵤ—(T)ᵥ—(CR¹⁴R¹⁵)ᵥᵥ—R⁷ wherein T is
CR¹⁴R¹⁵—CR¹⁴R¹⁵, CR'=CR' C≡C, or NR' and R¹⁴
and R¹⁵ are R', OR', or NR'R" provided that R¹⁴ and
R¹⁵ are not simultaneously OR' or NR'R' when they are attached to the same carbon;

R¹–R³ and R¹'–R³' are R* or R;

R⁶ is W—(CR'₂)ᵩ—Z—(CR'R¹⁰)ᵣ—U—(CR'₂)ₛ;

x is 0 to 2; and u, v and w independently are 0, 1, or 2.

More suitably,

A¹ is CR¹R¹', CR¹, NR¹, N, O or S;

A² is CR²R²', NR² or CR²;

A³ is CR³R³', NR³, N, O, or S;

D¹ and D⁴ are CH;

D² or D³ is CR⁶;

R² is R;

R³ or R³' is R*; and

R⁶ is W—(CR'²)ᵩ—Z—(CR'R¹⁰)ᵣ—U.

Suitably, (CR'R¹⁰)ᵣ—U—(CR'²)ₛ—V is CONR', NR'CO,
CH(NR'R")CONH, CH₂CONH, CONR'CH₂, CONHCH₂,
CH₂CHOH, CHOHCH₂, CONHCHR'CH₂,
CH₂NHCO₂CH₂, CH₂CH₂NHCO₂, CONHCH₂CO,
CONHCH₂CHOH, CH=CHCONH, NHCO₂CH=CH,
SO₂NR'CHR'CH₂, or CH=CH, or CH₂CH₂.

Representative compounds of this invention are given by each of formulae (II)–(VIII):

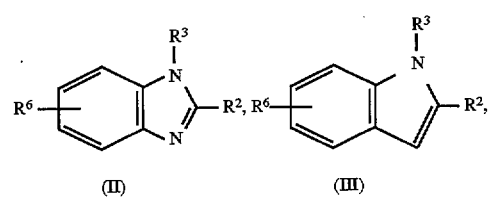

(II)        (III)

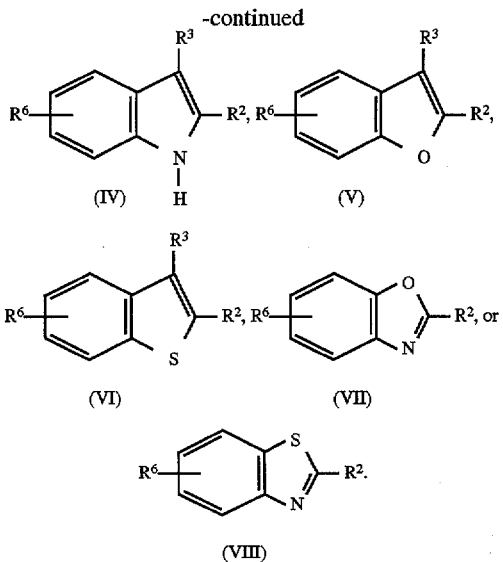

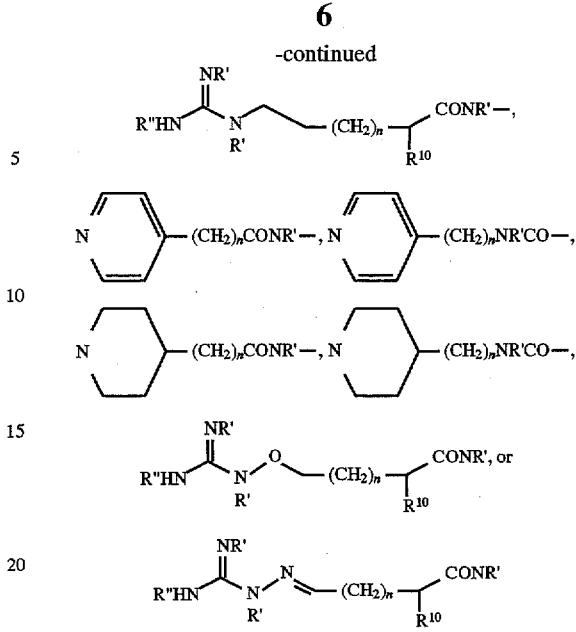

Preferably, $A^1$ is $CH_2$, $CH$, $NR''$, $N$, $O$, or $S$; $A^2$ is $CR^2$ or $CR^2R^{2'}$; and $A^3$ is $CR^3R^{3'}$, $CR^3$, $NR^{3'}$, $N$, $O$, or $S$.

Preferably, $R^1$ and/or $R^{1'}$ are absent or present as H.

Preferably, $R^2$ is $R^7$, —$CH_2R^7$, —$CH_2CH_2R^7$, —$CH_2CH_2CH_2R^7$, —$NHCH_2R^7$, or —$NHCH_2CH_2R^7$. Most preferably, $R^7$ is $CO_2H$.

Preferably, $R^3$ is absent or present as H or —$C_{1-6}$alkyl. Most preferably, Q is Ar.

Preferably, $(CR'R^{10})_r$—U—$(CR'_2)s$ is CONH or NHCO.

Preferably, Z is phenyl.

Preferably, W is R'R''N—, R'R''NC(=NR'), or R'R''NC(=NR')NR'—, R'R''NCO—, or (N) wherein R' and R'' are preferably H.

Most preferably, $R^6$ is

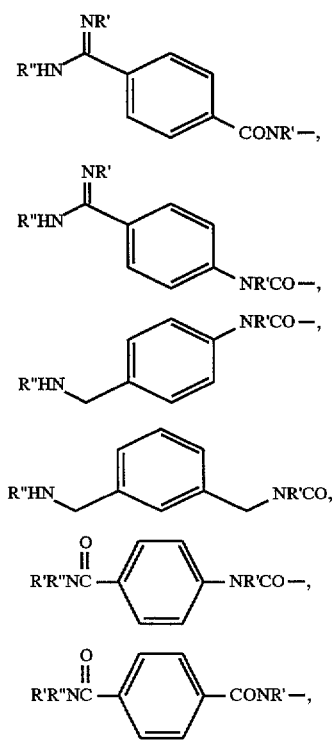

In one group of preferred compounds, $R^1$ is absent; $R^2$ is $CH_2CO_2H$, $CH_2CH_2CO_2H$, $CH_2CH_2CH_2CO_2H$, $NHCH_2CO_2^H$, or $NHCH_2CO_2H$; $R^3$ is H, $CH_2$—Ar, or $CH_2CH_2$—Ar; Z is phenyl; W is $H_2N$—, $H_2NC$(=NH)—, $H_2NCO$—, or $H_2NC$(=NH)NH—; and $(CR'R^{10})_r$—U—$(CR'_2)_s$—V is $CH_2NHCO$, $CH(NR'R'')CONH$, CONH, $N(CH_3)CO$ or NHCO.

Particular compounds of the invention include, but are not limited to, the following:

[5-(4-(aminoiminomethyl)benzoylamino]benzimidazole-2-amino-N-acetic acid;

[5-(4-aminoiminomethyl)benzoylamino]benzimidazole-2-amino-N-propanoic acid;

[5-(4-aminoiminomethyl)benzoylamino]benzimidazole-2-propanoic acid;

[5-(4-aminomethyl)benzoylamino]benzimidazole-2-amino-N-acetic acid;

[5-(4-aminoiminomethyl)phenylaminocarbonyl] benzimidazole-2-amino-N-acetic acid;

1-N-benzyl-[6-(4-aminoiminomethyl)benzoylamino] benzimidazole-2-propanoic acid;

1-N-benzyl-[5-(4-aminoiminomethyl)benzoylamino] benzimidazole-2-propanoic acid; and 1-N-phenethyl-[5-(4-aminoiminomethyl)benzoylamino] benzimidazole-2-propanoic acid;

or a pharmaceutically acceptable salt thereof.

The most preferred compound of this invention is [5-(4-aminoiminomethyl)benzoylamino]benzimidazole-2-propanoic acid or a pharmaceutically acceptable salt thereof.

In the above description of formula (I), preferably only one of $A^1$ to $A^3$ are substituted by R, and only one of $D^1$–$D^4$ is substituted by $R^6$. W represents a nitrogen-containing group which is capable of making a hydrogen bond: Preferably W is a basic nitrogen moiety. $R^7$ represents a group with a non-bonding pair of electrons which is capable of forming a hydrogen bond or chelating with a metal. Preferably $R^7$ is acidic. It is also preferred that 10–15 intervening covalent bonds via the shortest intramolecular path will exist between the group $R^7$ and W for optimal spacing between these groups, and the moieties T, U, V and Z, and the alkyl spacers represented by q, r, s, u, v and w are chosen accordingly.

Abbreviations and symbols commonly used in the peptide and chemical arts are used herein to describe the compounds of this invention. In general, the amino acid abbreviations follow the IUPAC-IUB Joint Commission on Biochemical Nomenclature as described in *Eur. J. Biochem.*, 158, 9 (1984).

Arg refers to arginine, MeArg refers to $N^\alpha$-methyl-arginine, HArg refers to homoarginine, NArg refers to norarginine, (Me2)Arg refers to N',N''-dimethyl arginine, (Et$_2$)Arg refers to N',N''-diethyl arginine and Orn refers to ornithine. These radicals are suitable components of the substituent $R^6$. $N^\alpha$-Substituted derivatives of these amino acid are also useful in this invention. Representative methods for preparing co-substituted derivatives are disclosed in U.S. Pat. No. 4,687,758; Cheung et al., *Can. J. Chem.*, 55, 906 (1977); Freidinger et al., *J. Org. Chem.*, 48, 77, (1982); and Shuman et al., PEPTIDES: PROCEEDINGS OF THE 7TH AMERICAN PEPTIDE SYMPOSIUM, Rich, D., Gross, E., Eds, Pierce Chemical Co., Rockford, Ill. ,617 ( 1981 ), which are incorporated herein by reference.

$C_{1-4}$alkyl as applied herein means carbon chains which are branched or unbranched and includes methyl, ethyl, n-propyl, isopropyl, n-butyl, isobutyl and t-butyl. $C_{1-6}$alkyl additionally includes pentyl, n-pentyl, isopentyl, neopentyl and hexyl and the simple aliphatic isomers thereof. $C_{0-4}$alkyl and $C_{0-6}$alkyl additionally indicates that no alkyl group need be present (e.g. that a covalent bond is present).

$C_{2-6}$alkenyl as applied herein means an alkyl group of 2 to 6 carbons wherein a carbon-carbon single bond is replaced by a carbon-carbon double bond. $C_{2-6}$alkenyl includes ethylene, 1-propene, 2-propene, 1-butene, 2-butene, isobutene and the several isomeric pentenes and hexenes. Both cis and trans isomers are included.

$C_{2-6}$alkynyl means an alkyl group of 2 to 6 carbons wherein one carbon-carbon single bond is replaced by a carbon-carbon triple bond. $C_{2-6}$alkynyl includes acetylene, 1-propyne, 2-propyne, 1-butyne, 2-butyne, 3-butyne and the simple isomers of pentyne and hexyne.

$C_{1-4}$oxoalkyl refers to an alkyl group of up to four carbons wherein a CH$_2$ group is replaced by a C(O), or carbonyl, group. Substituted formyl, acetyl, 1-propanal, 2-propanone, 3-propanal, 2-butanone, 3-butanone, 1- and 4-butanal groups are representative. C1-6oxoalkyl includes additionally the higher analogues and isomers of five and six carbons substituted by a carbonyl group. $C_{3-6}$oxoalkenyl and $C_{3-6}$oxoalkynyl refers to a $C_{3-6}$alkenyl or $C_{3-6}$alkynyl group wherein a CH$_2$ group is replaced by C(O) group. $C_{3-4}$oxoalkenyl includes 1-oxo-2-propenyl, 3-oxo-1-propenyl, 2-oxo-3-butenyl and the like.

$C_{1-4}$aminoalkyl as applied herein means an alkyl group of 1 to 4 carbon atoms that is attached to an amino group. $C_{1-4}$aminoalkyl includes aminomethyl, aminoethyl, aminopropyl, and aminobutyl. $C_{3-4}$alkenyl and $C_{3-4}$aminoalkynyl refer to a $C_{3-4}$alkynyl or $C_{3-4}$alkenyl group that is attached to an amino group. Q—$C_{1-4}$aminoalkyl group and the like refer to a $C_{1-4}$aminoalkyl group wherein in any position a carbon-hydrogen bond is replaced by a carbon-Q bond.

A substituent on a $C_{1-6}$alkyl, $C_{2-6}$alkenyl, $C_{2-6}$alkynyl, $C_{1-4}$aminoalkyl, or $C_{1-6}$ oxoalkyl group, such as $R^{11}$ or $R^7$, may be on any atom which results in a stable structure, and is available by conventional synthetic techniques.

Q—$C_{1-6}$alkyl refers to a $C_{1-6}$alkyl group wherein in any position a carbon-hydrogen bond is replaced by a carbon-Q bond. Q—$C_{2-6}$alkenyl and Q—$C_{2-6}$alkynyl have a similar meaning with respect to $C_{2-6}$alkenyl and $C_{2-6}$alkynyl.

Ar, or aryl, as applied herein, means phenyl or naphthyl, or phenyl or naphthyl substituted by one to three moieties $R^{11}$. In particular, $R^{11}$ may be $C_{1-4}$alkyl, $C_{1-4}$alkoxy, $C_{1-4}$alkthio, trifluoroalkyl, OH, Cl, Br or I.

Het, or heteroaryl, indicates an optionally substituted five or six membered aromatic ring, or a nine or ten-membered aromatic ring containing one to three heteroatoms chosen from the group of nitrogen, oxygen and sulfur, which are stable and available by conventional chemical synthesis. Illustrative heterocycles are imidazole, benzimidazole, pyrrole, indole, pyridinyl, quinoline, benzofuryl, furyl, benzopyranyl, benzothiophene or thiophene. Any accessible combination of up to three substituents, such as chosen from $R^{11}$, on the Het ring that is available by chemical synthesis and is stable is within the scope of this invention.

$C_{3-7}$cycloalkyl refers to an optionally substituted carbocyclic system of three to seven carbon atoms, which may contain up to two unsaturated carbon-carbon bonds. Typical of $C_{3-7}$cycloalkyl are cyclopropyl, cyclobutyl, cyclopentyl, cyclopentenyl, cyclohexyl, cyclohexenyl and cycloheptyl. Any combination of up to three substituents, such as chosen from $R^{11}$, on the cycloalkyl ring that is available by conventional chemical synthesis and is stable, is within the scope of this invention.

Any accessible substituted five-membered ring as referred to herein is any saturated or unsaturated five-membered ring which (i) has up to three substituents, such as R or R*, wherein the substituents may be present on any atom or heteroatom that results in a stable structure, and (ii) contains up to two heteroatoms selected from the group of N, O and S, wherein S and N may optionally be oxidized, and (iii) is stable and may be synthesized by one skilled in the chemical arts in a form fused via two adjacent ring carbon atoms to a phenyl, pyridyl, pyrazinyl, pyridazinyl or pyrimidinyl ring. Typical of accessible five-membered rings are the common saturated and unsaturated rings of cyclopentane, cyclopentene, furan, thiophene, imidazole, pyrrole, thiazole, and oxazole.

Any accessible substituted six-membered ring as referred to herein is an unsaturated (e.g. aromatic) six-membered ring which (i) has one to three substituents, such as chosen from $R^6$, (ii) optionally contains up to two nitrogens, (iii) is fused via two adjacent carbon atoms to any accessible substituted five-membered ring, and (iv) is stable and may be prepared by one skilled in the chemical arts. Typical of accessible six-membered rings are phenyl, pyridyl, pyrazinyl, pyridazinyl or pyrimidinyl ring. Representative bicyclic rings formed by the combination of the accessible six- and five-membered rings are: indene, isoindene, benzofuran, isobenzofuran, benzothiophene, isobenzothiophene, indole, indolenine, isobenzazole, 1,5-pyrindine, isoindazole, indoxazine, benzoxazole, anthranil, benzothiazole, and purine. Phenyl is a preferred accessible six-membered ring, and imidazole and pyrrole are preferred accessible five-membered rings. Thus, the preferred bicyclic rings formed by the combination of the accessible six- and five-membered rings are benzimidazole and indole.

It will be understood that, with respect to $A^1$–$A^3$, $CR^1R^{1'}$—$CR^3R^{3'}$ and $NR^1$–$NR^3$ are saturated sp$^3$ carbon and nitrogen atoms, respectively, which are singly bonded to the adjacent ring atoms; $CR^1R^{1'}$—$CR^3R^{3'}$ may also represent an sp$^2$ carbon atom. It will be further understood that, with respect to $A^1$–$A^3$, $CR^1$—$CR^3$ and N, they may represent an unsaturated sp$^2$ carbon or nitrogen atom, which may be connected by an endocyclic double bond to an adjacent atom in the ring, provided such arrangement results in the creation of a stable compound.

Ⓝ as used herein indicates a nitrogen heterocycle, which may be a saturated or an unsaturated stable five-, six- or seven-membered monocyclic ring, containing up to three nitrogen atoms or containing one nitrogen atom and a heteroatom chosen from oxygen and sulfur, and which may be substituted on any atom that results in a stable structure, and wherein the nitrogen heteroatom may be optionally quaternized. Representative of Ⓝ are pyrroline, pyrrolidine, imidazole, imidazoline, imidazolidine, pyrazole, pyrazoline, pyrazolidine, piperidine, piperazine, morpholine, pyridine, tetrahydropyridine, tetrahydro- and hexahydro-azepine. In particular, Ⓝ may be pyrrolidinyl, piperidinyl, tetrahydropyridinyl, or piperidinyl.

AA as referred to herein is an amino acid with its carboxyl group optionally protected, wherein the amino acid may be any of the natural amino acids or penicillamine. The unprotected carboxyl group is a free carboxylic acid group. Protecting groups for the carboxyl are esters or amides which are formed, for instance, when the OH of the carboxy group is replaced by $R^8$.

C(O) indicates a carbon doubly bonded to oxygen (eg. carbonyl), C(S) indicates a carbon doubly bonded to sulfur (eg. thiocarbonyl).

t-Bu refers to the tertiary butyl radical, Boc refers to the t-butyloxycarbonyl radical, Fmoc refers to the fluorenylmethoxycarbonyl radical, Ph refers to the phenyl radical, Cbz refers to the benzyloxycarbonyl radical, BrZ refers to the o-bromobenzyloxycarbonyl radical, ClZ refers to the o-chlorobenzyloxycarbonyl radical, Bzl refers to the benzyl radical, 4-MBzl refers to the 4-methyl benzyl radical, Me refers to methyl, Et refers to ethyl, Ac refers to acetyl, Alk refers to $C_{1-4}$alkyl, Nph refers to 1- or 2-naphthyl and cHex refers to cyclohexyl MeArg is $N^\alpha$-methyl arginine.

DCC refers to dicyclohexylcarbodiimide, DMAP refers to dimethylaminopyridine, DIEA refers to diisopropylethyl amine, EDC refers to N-ethyl-N'(dimethylaminopropyl) carbodiimide. HOBt refers to 1-hydroxybenzotriazole, THF refers to tetrahydrofuran, DIEA refers to diisopropylethylamine, DMF refers to dimethyl formamide, NBS refers to N-bromo-succinimide, Pd/C refers to a palladium on carbon catalyst, PPA refers to 1-propanephosphonic acid cyclic anhydride, DPPA refers to diphenylphosphoryl azide, BOP refers to benzotriazol-1-yloxy-tris(dimethylamino)phosphonium hexafluorophosphate, HF refers to hydrofluoric acid, TEA refers to triethylamine, TFA refers to trifluoroacetic acid, PCC refers to pyridinium chlorochromate.

The compounds of formula (I) are generally prepared by reacting a compound of the formula (IX) with a compound of the formula (X):

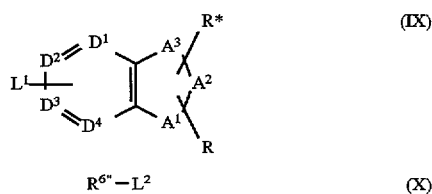

wherein $D^1$–$D^4$ and $A^1$–$A^3$, R and R* are as defined in formula (I), with any reactive functional groups protected;

$L^1$ and $L^1$ are functional groups which are capable of reacting to form the linkage —(CR'$R^{10}$)$_r$—U—(CR'$_2$)$_s$—V; and $R^{6"}$ is W—(CR'$_2$)$_q$—Z— and any portion of the group —(CR'$R^{10}$)$_r$—U—(CR'$_2$)$_s$—V— which is connected to $L^2$, with any reactive functional groups protected;

and thereafter removing any protecting groups, and
   optionally forming a pharmaceutically acceptable salt.

It will be apparent that the precise identity of $L^1$ and $L^2$ will be dependent upon the site of the linkage being formed. General methods for preparing the linkage —(CR'$R^{10}$)$_r$—U—(CR'$_2$)$_s$—V— are described for example, in EP-A 0 372 486 and EP-A 0 381 033 and EP-A 0 478 363, which are incorporated herein by reference.

For instance, if V is CONH, $L^1$ may be —NH$_2$, $L^2$ may be OH (as in an acid) or Cl (as in an acid chloride), and $R^{6"}$ may be W—(CR'$_2$)$_q$—Z—(CR'$R^{10}$)$_r$—U—(CR'$_2$)$_s$—C(O), with any functional groups optionally protected. For example, $R^{6"}$ may be (benzyloxycarbonyl-amidino)benzoyl- or ($N^\alpha$-Boc,$N^{guan}$-Tos)arginyl-. When $L^2$ is OH, a coupling agent is used.

Similarly, if V is NHCO, $L^1$ may be —CO$_2$H or CO—Cl, $L^2$ may be —NH$_2$, and $R^{6"}$ may be W—(CR'$_2$)$_q$—Z—(CR'$R^{10}$)$_r$—U—(CR'$_2$)$_s$—. For example, $R^{6"}$ may be (benzyloxycarbonyl-amidino)phenyl, (benzyloxycarbonylamino)methylbenzyl- or 6-(benzyloxycarbonylamino)hexyl-.

When V is NHSO$_2$, $L^1$ may be SO$_2$Cl, $L^2$ may be —NH$_2$ and $R^{6"}$ may be as above. When V is SO$_2$NH, $L^1$ may be —NH$_2$ and $L^2$ may be SO$_2$Cl. Methods to prepare such sulfonyl chlorides are disclosed, for instance, in *J. Org. Chem.*, 23, 1257 (1958).

If V is CH═CH, $L^1$ may be —CHO, $L^2$ may be CH═P—Ph$_3$ and $R^{6"}$ may be W(CR'$_2$)$_q$—Z—(CR'$R^{10}$)$_r$—U—(CR'$_2$)$_s$—.

Where V is CH$_2$CH$_2$ may be obtained by reduction of a suitably protected compound wherein V is CH═CH.

When V is CH$_2$O, CH$_2$N or, $L^1$ may be —OH, —NH or —, respectively; $L^2$ may be —Br; and $R^{6"}$ may be W—(CR'$_2$)$_q$—Z—(CR'$R^{10}$)$_r$—U—(CR'$_2$)$_s$—. For example, $R^{6"}$ may be (benzyloxycarbonylamino)-methylbenzyl- or 2-(N-benzyl-4-piperidinyl)ethyl. Similarly when U or V is OCH$_2$, NR'CH$_2$ or, $L^1$ may be —CH$_2$Br, and $L^2$ may be —OH, —NH or —, respectively.

Compounds wherein V is CHOHCH$_2$ may be prepared from a suitably protected compound where V is CH═CH by the procedure disclosed in *J. Org. Chem.*, 54, 1354 (1989).

Compounds wherein V is CH$_2$CHOH may be obtained from a suitably protected compound where V is CH═CH by hydroboration and basic oxidation as disclosed in *Tet. Lett.*, 31, 231 (1990).

The compounds of formula (IX), wherein $A^1$ and $A^3$ are nitrogen and the five-membered ring is unsaturated, are benzimidazoles and are prepared by the general methods illustrated by Schemes I–III. The compounds of formula (IX), wherein A' is carbon and $A^3$ is nitrogen and the five-membered ring is unsaturated, are indoles. These compounds are prepared by the procedure illustrated in Scheme IV. The compounds of Formula (IX), wherein $A^1$ is nitrogen and $A^3$ is oxygen or sulfur and the five-membered ring is unsaturated, are benzoxazoles and benzothiazoles, respectively, and are prepared by the methods detailed in Nestor, et al., *J. Med. Chem.*, 27:320–325 (1984)). Conversion of these benzoxazoles and benzothiazoles to Formula (I) compounds is carried out using the methods described hereinbelow for the preparation of Formula (I) benzimidazoles and indoles. In the Schemes $R^{1"}$–$R^{7"}$ indicate $R^1$–$R^7$ or a suitable precursor thereof, wherein any functional groups are protected as known in the art.

Scheme I

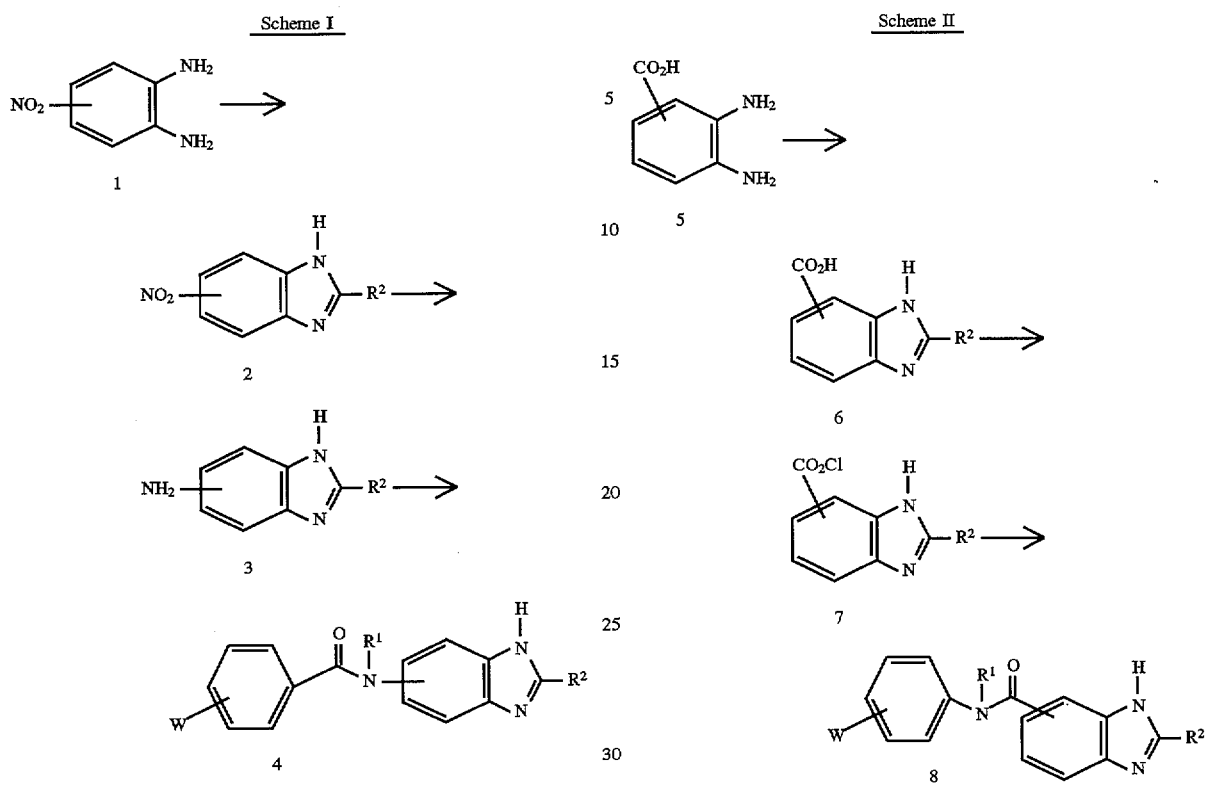

Scheme I provides a method of preparing compounds wherein $A^1$ and $A^3$ are nitrogen and $A^2$ is $CR^2$. Generally, the synthesis is begun with a substituted 1,2-diaminobenzene compound. For compounds wherein $(CR'R^{10})_r$—U—$(CR'_2)_s$—V— is CONR'— the diaminobenzene starting material is substituted further by a nitro group. Reaction of this compound with an appropriately substituted isothiocyanate, such as methyl isothiocyanatopropionate or methyl isothiocyanatoacetate, or an appropriately substituted carboxylic acid compound, such as mono-methyl succinate, yields the fused 6-5 benzimidazole ring system with the $R^2$-substituent introduced. Reduction of the nitro group, such as with hydrogen in the presence of a catalyst, for example, palladium or carbon, in an acetic medium, for example in acetic acid/methanol (1:1), results in the formation of the corresponding amino compound. Condensation of the amino group with a carboxylic acid of the formula, W—$(CR'_2)_q$—Z—$CO_2H$, such as with 4-(Cbz-aminoiminomethyl)benzoic acid or 4-(Boc-aminomethyl)benzoic acid, in the presence of an amide-forming agent, such as in the presence of N-ethyl-N'(dimethylaminopropyl) carbodiimide and 1-hydroxybenzotriazole, and a base, such as diisopropylethyl amine, in a suitable solvent, such as in dimethylformamide. Protective groups, such as those for amino or carboxyl groups, are selectively removed by methods known in the art. For example, a Cbz-group on a nitrogen atom may be removed by hydrogenation in the presence of a catalyst, such as palladium on carbon, in an acidic medium, such as in acetic acid/methanol, and a Boc-group on a nitrogen atom and/or an ester group on a carboxylic acid may be removed by acid, for example refluxing aqueous acetic acid.

Scheme II provides a method of preparing compounds wherein $A^1$ and $A^3$ are nitrogen, $A^2$ is $CR^2$ and $(CR^1R^{10})_r$—U—$(CR'_2)_s$—V— is NR'CO—. According to this scheme, a 1,2-diaminobenzene compound substituted by a carboxylic acid is reacted with an appropriately substituted isothiocyanate to give $R^2$-substituted benzimidazole compounds. The carboxylic acid group is then converted to the corresponding acid chloride using, for example, refluxing thionyl chloride and then the acid chloride is reacted with an amine of the formula, W—$(CR'_2)_q$—Z—$NH_2$, such as 4-(Cbz-aminoiminomethyl)aniline, in the presence of a base, such as triethylamine, in an appropriate solvent, such as methylene chloride and dimethylformamide. The amino and carboxyl protecting groups are removed by methods known in the art and by methods as described hereinbefore.

Scheme III

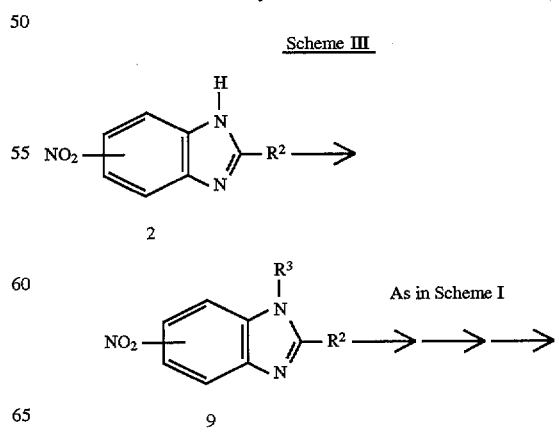

-continued
Scheme III

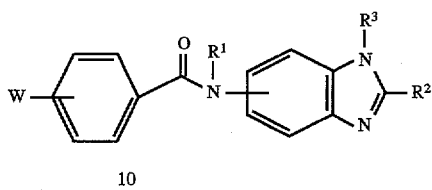

10

Scheme III provides a method of preparing compounds wherein $A^1$ is N, $A^2$ is $CR^2$, $A^3$ is $NR^3$ and $(CR'R^{10})_r$—U—$(R'_2)_s$—V— is CONR'—. According to this scheme, the Scheme I, Formula 2, benzimidazole compounds are reacted with an $R^3$-substituted halide, such as benzyl bromide, in the presence of a base, such as sodium hydride, in a suitable solvent, such as dimethylformamide. These tri-substituted benzimidazoles are then convened to Formula (I) compounds as detailed in Scheme I, Formulae 2 to 4.

Scheme IV

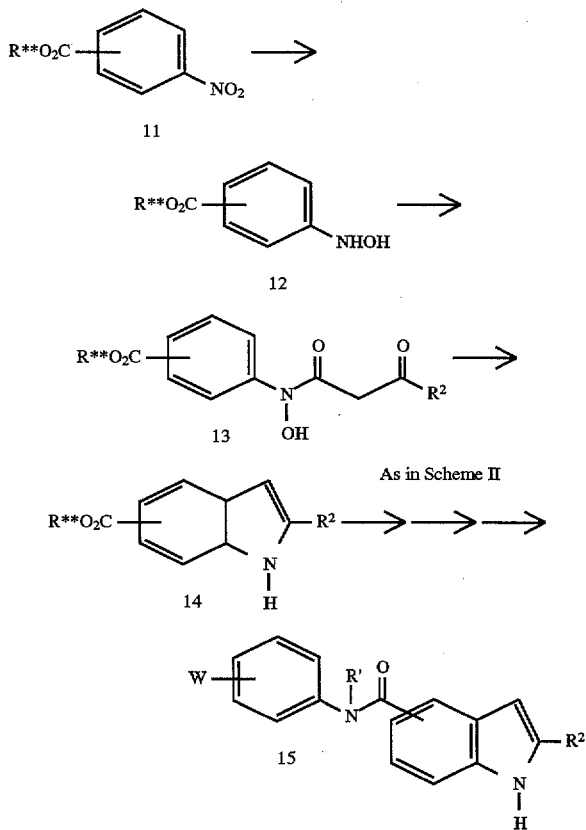

Scheme IV provides a method of preparing compounds wherein $A^1$ is carbon, $A^2$ is $CR^2$, $A^3$ is nitrogen, and $(CR'R^{10})_r$—U—$(CR'_2)_s$—V— is NR'CO—. According to this scheme, the nitro group of a nitrobenzoate ester, such as benzyl 4-nitrobenzoate, is converted to the corresponding hydroxyamino group using, for example, hydrazine hydrate in the presence of a reducing agent, such as wet rhodium on carbon, in a suitable solvent, such as tetrahydrofuran. Reaction of the hydroxyamino group with an $R^2$-substituted acyl Meldrum's acid (Meldrum's acid is 2,2-dimethyl-1,3-dioxane-4,6-dione.) in an appropriate solvent, such as acetonitrile, yields N-acetoacetylation of the N-phenyl hydroxylamine intermediate.. The $R^2$-substituted-carboxyindole is prepared from this intermediate using, for example, 2,2'-azobisisobutyronitrile (AIBN), in an appropriate deoxygenated solvent, such as xylene. The ester protecting group on the indole carboxylic acid group is removed by conventional methods, such as, when a benzyl ester is present, by hydrogenation in the presence of a suitable catalyst, such as palladium on carbon. Formula (I) compounds are prepared as detailed in Scheme II, formulae 6 to 8.

Coupling reagents as used herein denote reagents which may be used to form peptide bonds. Typical coupling methods employ carbodiimides, activated anhydrides and esters and acyl halides. Reagents such as EDC, DCC, DPPA, PPA, BOP reagent, HOBt, N-hydroxysuccinimide and oxalyl chloride are typical.

Coupling methods to form peptide bonds are generally well known to the art.

The methods of peptide synthesis generally set forth by Bodansky et al., THE PRACTICE OF PEPTIDE SYNTHESIS, Springer-Verlag, Berlin, 1984, Ali et al. in J. Med. Chem., 29, 984 (1986) and J. Med. Chem., 30, 2291 (1987) are generally illustrative of the technique and are incorporated herein by reference.

Solution synthesis for the formation of amide or peptide bonds is accomplished using conventional methods used to form amide bonds. Typically, the amine or aniline is coupled via its free amino group to an appropriate carboxylic acis substrate using a suitable carbodiimide coupling agent, such as N,N' dicyclohexyl carbodiimide (DCC), optionally in the presence of catalysts such as 1-hydroxybenzotriazole (HOBO and dimethylamino pyridine (DMAP). Other methods, such as the formation of activated esters, anhydrides or acid halides, of the free carboxyl of a suitably protected acid substrate, and subsequent reaction with the free amine of a suitably protected amine, optionally in the presence of a base, are also suitable. For example, a protected Boc-amino acid or Cbz-amidino benzoic acid is treated in an anhydrous solvent, such as methylene chloride or tetrahydrofuran(THF), in the presence of a base, such as N-methyl morpholine, DMAP or a trialkylamine, with isobutyl chloroformate to form the "activated anhydride", which is subsequently reacted with the free amine of a second protected amino acid or aniline.

Compounds of formula (X) are prepared by conventional methods known in the art from commercially available materials. W is a generally a basic functional group attached to Z, optionally via an alkyl chain, and is protected during the synthesis of $R^6$ or is introduced into the molecule after the $—(CR'R^{10})_r—U—(CR'_2)_s—V—$ linkage has been formed. For example, compounds of formula (x) or formula (I) wherein W is a suitably substituted R'R"N—, R"R'NC(=NR'), R'$_2$N(R$^{13}$)C=N—, R"N=(R$^{13}$)C—NR'—, R'$_2$N—(R$_2$N)C=N— or R"R'N(R'N=)C—NR', are prepared by conventional methods including those disclosed in EP-A 0 372 486, EP-A 0 381 033 or EP-A 0 478 363, which are incorporated herein by reference.

Compounds of formula (X) wherein W is Ⓝ are prepared, inter alia, by methods disclosed in EP-A 0 478 363.

Compounds W is R'$_2$N(R'$_2$N)C=N—X— or R"R'N=)C—NR'—X—, and X is O are prepared, inter alia, by methods disclosed in J. Org. Chem., 51, 5047 (1986).

Compounds wherein W is R'$_2$N(R'$_2$N)C—N—X— or R"R'N(R'N=)C—NR'—X—, and X is N=CR', are prepared, inter alia, by methods disclosed in United States Pat. No. 3,714,253 and Eur. J. Med. Chem.-Chim. Ther., 20, 25 (1985).

Compounds wherein W is R'$_2$N(R'$_2$N)C=N—X— or R"R'N(R'N=)C—NR'—X—, and X is C(O), are prepared, inter alia, by methods disclosed in U.S. Pat. No. 3,714,253 and *Can. J. Chem.*, 43, 3103 (1965).

Compounds wherein W is R'$_2$NR'C(=NR')— may be prepared, inter alia, by methods disclosed in *J. Het. Chem.*, 16, 1063 (1979) or *J. Her. Chem.*, 26, 125 (1989).

Compounds wherein W is R'$_2$NR'NC(—NR')— are prepared by conventional methods including those disclosed in Syn., 583 (1974).

Compounds wherein W is R'R"NR'N— are prepared, inter alia, by methods disclosed in *J. Prakt. Chem.*, 36, 29 (1967).

Compounds wherein W is R'R"NR'NCO— are prepared, inter alia, by methods disclosed in *Bull. Chem. Soc. Jpn.*, 43, 2257 (1970).

Compounds wherein W is R"R'NC(=NR')Y, and Y is S, are prepared, inter alia, by methods disclosed in *Chem. Lett.*, 1379 (1986).

Compounds of formula (X) or formula (I), wherein W is R"R'NC(=NR')Y and Y is O, are prepared by conventional methods including those disclosed in Japanese Patent 2022751.

The reactive functional groups of the sidechains of each synthetic fragment are suitably protected as known in the art. Suitable protective groups are disclosed in Green, PROTECTIVE GROUPS IN ORGANIC CHEMISTRY, John Wiley and Sons, New York, 1981. For example, the Boc, Cbz, phthaloyl or Fmoc group may be used for protection of an amino or amidino group. The Boc group is generally preferred for protection of an α-amino group. A t-Bu, cHex or benzyl ester may be used for the protection of the side chain carboxyl. A benzyl group or suitably substituted benzyl group (eg. 4-methoxy-benzyl or 2,4-dimethoxy-benzyl) is used to protect the mercapto group or the hydroxyl group. The tosyl group may be used for protection of the imidazolyl group and tosyl or nitro group for protection of the guanidino group. A suitably substituted carbobenzyloxy group or benzyl group may be also be used for the hydroxyl group or amino group. Suitable substitution of the carbobenzyloxy or benzyl protecting groups is ortho and/or para substitution with chloro, bromo, nitro or methyl, and is used to modify the reactivity of the protective group. Except for the Boc group, the protective groups for the amino moiety are, most conveniently, those which are not removed by mild acid treatment. These protective groups are removed by such methods as catalytic hydrogenation, sodium in liquid ammonia or I-IF treatment, as known in the art.

Modification of amino groups especially on the six-membered ring of the bicyclic system, may be accomplished by alkylation, sulfonylation, cyanation or acylation as is generally known in the art.

Acid addition salts of the compounds of formula (I) are prepared in a standard manner in a suitable solvent from the parent compound and an excess of an acid, such as hydrochloric, hydrobromic, sulfuric, phosphoric, acetic, maleic, succinic or methanesulfonic. The acetate salt form is especially useful. Certain of the compounds form inner salts or zwitterions which may be acceptable. Cationic salts are prepared by treating the parent compound with an excess of an alkaline reagent, such as a hydroxide, carbonate or alkoxide, containing the appropriate cation; or with an appropriate organic amine. Cations such as Li+, Na+, K+, Ca++, Mg++ and NH$_4$+ are specific examples of cations present in pharmaceutically acceptable salts.

This invention provides a pharmaceutical composition which comprises a compound according to formula (I) and a pharmaceutically acceptable carrier. Accordingly, the compounds of formula (I) may be used in the manufacture of a medicament. Pharmaceutical compositions of the compounds of formula (I) prepared as hereinbefore described may be formulated as solutions or lyophilized powders for parenteral administration. Powders may be reconstituted by addition of a suitable diluent or other pharmaceutically acceptable carrier prior to use. The liquid formulation may be a buffered, isotonic, aqueous solution. Examples of suitable diluents are normal isotonic saline solution, standard 5% dextrose in water or buffered sodium or ammonium acetate solution. Such formulation is especially suitable for parenteral administration, but may also be used for oral administration or contained in a metered dose inhaler or nebulizer for insufflation. It may be desirable to add excipients such as polyvinylpyrrolidone, gelatin, hydroxy cellulose, acacia, polyethylene glycol, mannitol, sodium chloride or sodium citrate.

Alternately, these compounds may be encapsulated, tableted or prepared in a emulsion or syrup for oral administration. Pharmaceutically acceptable solid or liquid carriers may be added to enhance or stabilize the composition, or to facilitate preparation of the composition. Solid carriers include starch, lactose, calcium sulfate dihydrate, terra alba, magnesium stearate or stearic acid, talc, pectin, acacia, agar or gelatin. Liquid carriers include syrup, peanut oil, olive oil, saline and water. The carrier may also include a sustained release material such as glyceryl monostearate or glyceryl distearate, alone or with a wax. The amount of solid carrier varies but, preferably, will be between about 20 mg to about 1 g per dosage unit. The pharmaceutical preparations are made following the conventional techniques of pharmacy involving milling, mixing, granulating, and compressing, when necessary, for tablet forms; or milling, mixing and filling for hard gelatin capsule forms. When a liquid carrier is used, the preparation will be in the form of a syrup, elixir, emulsion or an aqueous or non-aqueous suspension. Such a liquid formulation may be administered directly p.o. or filled into a soft gelatin capsule.

For rectal administration, the compounds of this invention may also be combined with excipients such as cocoa butter, glycerin, gelatin or polyethylene glycols and molded into a suppository.

This invention also provides a method of inhibiting platelet aggregation and clot formation in a mammal, especially a human, which comprises the internal administration of a peptide of formula (I) and a pharmaceutically acceptable carrier. Indications for such therapy include acute myocardial infarction (AMI), deep vein thrombosis, pulmonary embolism, dissecting anurysm, transient ischemia attack (TIA), stroke and other infarct-related disorders, and unstable angina. Chronic or acute states of hyper-aggregability, such as disseminated intravascular coagulation (DIC), septicemia, surgical or infectious shock, post-operative and post-partum trauma, cardiopulmonary bypass surgery, incompatible blood transfusion, abruptio placenta, thrombotic thrombocytopenic purpura (TTP), snake venom and immune diseases, are likely to be responsive to such treatment. In addition, the compounds of this invention may be useful in a method for the prevention of metastatic conditions, the prevention or treatment of fungal or bacterial infection, inducing immunostimulation, and the prevention or treatment of diseases in which bone resorption is a factor.

The compounds of this invention are administered either orally or parenterally to the patient, in a manner such that the concentration of drug in the plasma is sufficient to inhibit platelet aggregation, or other such indication. The pharmaceutical compositions containing the compounds of this invention are administered at a dose between about 0.2 to about 50 mg/kg in a manner consistent with the condition of the patient. For acute therapy, parenteral administration is preferred. For persistent states of hyperaggregability, an intravenous infusion of the compound in 5% dextrose in water or normal saline is most effective, although an intramuscular bolus injection may be sufficient.

For chronic, but noncritical, states of platelet aggregability, oral administration of a capsule or tablet, or a bolus intramuscular injection is suitable. The compounds of this invention are administered one to four times daily at a level of about 0.4 to about 50 mg/kg to achieve a total daily dose of about 0.4 to about 200 mg/kg/day.

This invention further provides a method for inhibiting the reocclusion of an mew or vein following fibrinolytic therapy, which comprises internal administration of a compound of formula (I) and a fibrinolytic agent. It has been found that administration of certain compounds in fibrinolytic therapy either prevents reocclusion completely or prolongs the time to reocclusion.

When used in the context of this invention the term fibrinolytic agent is intended to mean any compound, whether a natural or synthetic product, which directly or indirectly causes the lysis of a fibrin clot. Plasminogen activators are a well known group of fibrinolytic agents. Useful plasminogen activators include, for example, anistreplase, urokinase (UK), pro-urokinase (pUK), streptokinase (SK), tissue plasminogen activator (tPA) and routants, or variants, thereof, which retain plasminogen activator activity, such as variants which have been chemically modified or in which one or more amino acids have been added, deleted or substituted or in which one or more or functional domains have been added, deleted or altered such as by combining the active site of one plasminogen activator with the fibrin binding domain of another plasminogen activator or fibrin binding molecule. Other illustrative variants include tPA molecules in which one or more glycosylation sites have been altered. Preferred among plasminogen activators are variants of tPA in which the primary amino acid sequence has been altered in the growth factor domain so as to increase the serum half-life of the plasminogen activator. tPA Growth factor variants are disclosed, e.g., by Robinson et al., EP-A 0 297 589 and Browne et al., EP-A 0 240 334. Other variants include hybrid proteins, such as those disclosed in EP 0 028 489, EP 0 155 387 and EP 0 297 882, all of which are incorporated herein by reference. Anistreplase is a preferred hybrid protein for use in this invention. Fibrinolytic agents may be isolated from natural sources, but are commonly produced by traditional methods of genetic engineering.

Useful formulations of tPA, SK, UK and pUK are disclosed, for example, in EP-A 0 211 592, EP-A 0 092 182 and U.S. Pat. No. 4,568,543, all of which are incorporated herein by reference. Typically the fibrinolytic agent may be formulated in an aqueous, buffered, isotonic solution, such as sodium or ammonium acetate or adipate buffered at pH 3.5 to 5.5. Additional excipients such as polyvinyl pyrrolidone, gelatin, hydroxy cellulose, acacia, polyethylene, glycol, mannitol and sodium chloride may also be added. Such a composition can be lyophilized.

The pharmaceutical composition may be formulated with both the compound of formula (I) and fibrinolytic in the same container, but formulation in different containers is preferred. When both agents are provided in solution form they can be contained in an infusion/injection system for simultaneous administration or in a tandem arrangement.

Indications for such therapy include myocardial infarction, deep vein thrombosis, pulmonary embolism, stroke and other infarct-related disorders. The compound of this invention is administered just prior to, at the same time as, or just after patenteral administration of tPA or other fibrinolytic agent. It may prove desirable to continue treatment with the claimed compounds for a period of time well after reperfusion has been established to maximally inhibit post-therapy reocclusion. The effective dose of tPA, SK, UK or pUK may be from 0.5 to 5 mg/kg and the effective dose of the peptide may be from about 0.1 to 25 mg/kg.

For convenient administration of the inhibitor and the fibrinolytic agent at the same or different times, a kit is prepared, comprising, in a single container, such as a box, carton or other container, individual bottles, bags, vials or other containers each having an effective mount of the inhibitor for parenteral administration, as described above, and an effective amount of tPA, or other fibrinolytic agent, for parenteral administration, as described above. Such kit can comprise, for example, both pharmaceutical agents in separate containers or the same container, optionally as lyophilized plugs, and containers of solutions for reconstitution. A variation of this is to include the solution for reconstitution and the lyophilized plug in two chambers of a single container, which can be caused to admix prior to use. With such an arrangement, the fibrinolytic and the compound of this invention may be packaged separately, as in two containers, or lyophilized together as a powder and provided in a single container.

When both agents are provided in solution form, they can be contained in an infusion/injection system for simultaneous administration or in a tandem arrangement. For example, the platelet aggregation inhibitor may be in an i.v. injectable form, or infusion bag linked in series, via tubing, to the fibrinolytic agent in a second infusion bag. Using such a system, a patient can receive an initial bolus-type injection or infusion of the inhibitor followed by an infusion of the fibrinolytic agent.

The pharmacological activity of the compounds of this invention is assessed by their ability to inhibit the binding of 3H-SK&F 107260, a known RGD-fibrinogen antagonist, to the GPIIbIIIa receptor, their ability to inhibit platelet aggregation, in vitro, and their ability to inhibit thrombus formation in vivo.

Inhibition of RGD-mediated GPIIb-IIIa Binding

Purification of GPIIb-IIIa

Ten units of outdated, washed human platelets (obtained from Red Cross) were lyzed by gentle stirring in 3% octylglucoside, 20 mM Tris-HCl, pH 7.4, 140 mM NACl, 2 mM $CaCl_2$ at 4° C. for 2 h. The lysate was centrifuged at 100,000 g for 1 h. The supernatant obtained was applied to a 5 mL lentil lectin sepharose 4B column (E. Y. Labs) preequilibrated with 20 mM Tris-HCl, pH 7.4, 100 mM NACl, 2 mM $CaCl_2$, 1% octylglucoside (buffer A). After 2 h incubation, the column was washed with 50 mL cold buffer A. The lectin-retained GPIIb-IIIa was eluted with buffer A containing 10% dextrose. All procedures were performed at 4° C. The GPIIb-IIIa obtained was >95% pure as shown by SDS polyacrylamide gel electrophoresis.

Incorporation of GPIIb-IIIa in Liposomes

A mixture of phosphatidylserine (70%) and phosphatidylcholine (30%) (Avanti Polar Lipids) were dried to the walls of a glass tube under a stream of nitrogen. Purified GPIIb-IIIa was diluted to a final concentration of 0.5 mg/mL and mixed with the phospholipids in a protein:phospholipid ratio of 1:3 (w:w). The mixture was resuspended and sonicated in a bath sonicator for 5 min. The mixture was then dialyzed overnight using 12,000–14,000 molecular weight cutoff dialysis tubing against a 1000-fold excess of 50 mM Tris-HCl, pH 7.4, 100 mM NACl, 2 mM $CaCl_2$ (with 2 changes). The GPIIb-IIIa-containing liposomes wee centrifuged at 12,000 g for 15 min and resuspended in the dialysis buffer at a final protein concentration of approximately 1 mg/mL. The liposomes were stored at −70° C. until needed.

Competitive Binding to GPIIb-IIIa

The binding to the fibrinogen receptor (GPIIb-IIIa) was assayed by an indirect competitive binding method using [$^3$H]-SK&F-107260 as an RGD-type ligand. The binding assay was performed in a 96-well filtration plate assembly (Millipore Corporation, Bedford, Mass.) using 0.22 um hydrophilic durapore membranes. The wells were precoated with 0.2 mL of 10 µg/mL polylysine (Sigma Chemical Co., St. Louis, Mo.) at room temperature for 1 h to block nonspecific binding. Various concentrations of unlabeled benzadiazapines were added to the wells in quadruplicate. [$^3$H]-SK&F-107260 was applied to each well at a final concentration of 4.5 nM, followed by the addition of 1 µg of the purified platelet GPIIb-IIIa-containing liposomes. The mixtures were incubated for 1 h at room temperature. The GPIIb-IIIa-bound [$^3$H]-SK&F-107260 was seperated from the unbound by filtration using a Millipore filtration manifold, followed by washing with ice-cold buffer (2 times, each 0.2 mL). Bound radioactivity remaining on the filters was counted in 1.5 mL Ready Solve (Beckman Instruments, Fullerton, Calif.) in a Beckman Liquid Scintillation Counter (Model LS6800), with 40% efficiency. Nonspecific binding was determined in the presence of 2 µM unlabeled SK&F-107260 and was consistently less than 0.14% of the total radioactivity added to the samples. All data points are the mean of quadruplicate determinations. The compounds of this invention inhibit [$^3$H]-SK&F 107260 binding with Ki in the range of about 40 nM to about 50 µM. Preferred compounds have Ki of less than 100 nM.

Inhibition of Platelet Aggregation

Blood was collected (citrated to prevent coagulation) from, naive, adult mongrel dogs. Platelet rich plasma, PRP, was prepared by centrifugation at 150×g for 10 min at room temperature. Washed platelets were prepared by centrifuging PRP at 800×g for 10 min. The cell pellet thus obtained was washed twice in Tyrode's buffer (pH 6.5) without $Ca^{++}$ and resuspended in Tyrode's buffer (pH 7.4) containing 1.8 mM $Ca^{++}$ at 3×10$^5$ cells/ml. Compounds were added 3 min prior to the agonist in all assays of platelet aggregation. Final agonist concentrations were 0.1 unit/ml thrombin and 2 mM ADP (Sigma). Aggregation was monitored in a Chrono-Log Lumi-Aggregometer. Light transittance 5 min after addition of the agonist was used to calculate percent aggregation according to the formula % aggregation=[(90-CR) Ö(90-10)]×100, where CR is the chart reading, 90 is the baseline, and 10 is the PRP blank reading. IC50's were determined by plotting [% inhibition of aggregation] vs. [concentration of compound]. Compounds were assayed at 200 mM and diluted sequentially by a factor of 2 to establish a suitable dose response curve.

The compounds of this invention inhibit the aggregation of human platelets stimulated with ADP with IC50 of about 0.45 to about 50 µM. Preferred compounds have IC50 of less than 1 µM.

To assess the stability of the compounds to plasma proteases, the compounds were incubated for 3 h (rather than 3 min) in the PRP prior to addition of the agonist.

In Vivo Inhibition of Platelet Aggregation

In vivo inhibition of thrombus formation is demonstrated by recording the systemic and hemodynamic effects of infusion of the peptides into anesthetized dogs according to the methods described in Aiken et al., *Prostaglandins*, 19, 629 (1980).

The examples which follow are intended to in no way limit the scope of this invention, but are provided to illustrate how to make and use the compounds of this invention. Many other embodiments will be readily apparent and available to those skilled in the art.

EXAMPLES

Example 1

[5-(4-Aminoiminomethyl)benzoylamino] benzimidazole-2-amino-N-acetic Acid (i) Methyl 2-amino-N-acetate 5-nitrobenzimidazole Under argon, 4-nitro-1,2-phenylenediamine (7.15 g, 46.7 mmol) and methyl 2-isothiocyanatoacetate ( 6.12 g, 46.7 mmol) were mixed in dimethylformide (20 mL) and toluene (100 mL). The reaction was stirred at 65° C. for 45 minutes before cooling down to room temperature and adding mercuric oxide (10.13 g, 46.7 mmol) in one portion. The reaction was stirred at 65° C. overnight to give a dark brown solution. The reaction was filtered and rinsed with hot methanol, concentrated in vacuo to give a brownish-red oil. Flash chromatography (methanol/methylene chloride, 1:9) afforded the desired product (11.25 g, 96%).

(ii) Methyl 2-amino-N-acetate-5-aminobenzimidazole, acetate salt

The compound of Example 1(i) (4.04 g, 16.14) was dissolved in methanol acetic acid (50:50 mL) and then 10% palladium on carbon (1.5 g) was added. The reaction was hydrogenated at 45 psi for 2.5 hours, filtered through Celite®, rinsed with methanol, and concentrated under vacuo to give the desired product (3.65 g, 81%), which was used without further purification.

(iii) [5-(4-Cbz-aminoiminomethyl)benzoylamino] benzimidazole-2-amino-N-acetate, methyl ester The compound of Example 1(ii) (0.52 g, 1.86 mmol) was mixed with 4-(Cbz-aminoiminomethyl)benzoic acid (0.55 g, 1.86 mmol), 1-hydroxybenzotriazole (0.3 g 2.22 mmol), and N-ethyl-N'(dimethylaminopropyl)carbodiimide (0.43 g, 2.21 mmol) in dimethylformamide (12 mL). The reaction mixture was cooled down to 0° C. before adding diisopropylethylamine (0.74 g, 5.74 mmol) slowly, and then it was stirred at room temperature under argon overnight. The dark brown reaction mixture was poured into a flask containing 50 mL of ice and 5% sodium bicarbonate (6.8 mL) to give a white precipitate which was filtered and washed with cold water to give, upon drying, the desired product (0.68 g, 73%) that was used without further purification.

(iv) [5-(4-Aminoiminomethyl)benzoylamino] benzimidazole-2-amino-N-acetate methyl ester, acetate salt Starting with the compound of Example 1(iii), the title compound was prepared following the procedure for the preparation of the compound of Example 1(ii).

(v) [5-(4-Aminoiminomethyl)benzoylamino] benzimidazole-2-amino-N-acetic acid, trifluoroacetic acid salt The compound of Example 1(iv) (0.25 g, 0.12 mmol) was mixed in 10% acetic acid (12 mL) and stirred at 110° C. overnight. The solvent was removed under vacuo to give the crude product (0.11 g, 94%). Purification on reverse phase prep HPLC (CH$_3$CN:H$_2$O, 0.1% TFA) afforded the analytically pure desired product. ESMS: m/e 353.2 (M+H)$^+$, 351.0 (M−H)$^-$. Anal. Calcd. for C$_{17}$H$_{16}$N$_6$O$_3$.2C$_2$HF$_3$O$_2$.½H$_2$O; C,42.79; H, 3.25; N, 14.26. Found: C, 42.84; H, 3.04; N, 14.00.

Example 2

[5-(4-Aminoiminomethyl)benzoylamino] benzimidazole-2-amino-N-propionic Acid (i) Methyl 3-isothiocyanatopropionate To β-alanine methyl esterhydrochloric acid salt suspended in methylene chloride (60 mL) was added triethylamine (10.87 g, 107.4 mmol). The reaction mixture was cooled downed to −15° C. before adding carbon disulfide (4.1 g, 53.8 mmol) dissolved in chloromethane (30 mL) dropwise over 25 minutes. The reaction was warmed to 10° C. and stirred for 10 minutes. before lowering the temperature to 0° C. and adding ethyl chloroformate (5.83 g, 53.7 mmol) dissolved in chloromethane (5 mL) dropwise over 15 minutes. The temperature was increased to room temperature and stirred for 20 minutes before lowering to 0° C. Triethylamine (5.43 g, 53.7 mmol) was then added. The temperature was increased to room temperature and then stirred for 30 minutes. The reaction mixture was washed with water (50 mL), 1N hydrochloric acid (50 mL), 5% sodium bicarbonate and water (50 mL), dried over magnesium sulfate, filtered and concentrated under vacuo to give 7.3 g. of crude product. Flash chromatography (ethyl acetate/hexane, 1:4) afforded the desired product (4.03 g, 52%).

(ii) Methyl 2-amino-N-propanoate-5-nitrobenzimidazole

Starting with the compound of Example 2(i), the title compound was prepared following the procedure of Example 1(i).

(iii) Methyl 2-amino-N-propanoate 5-aminobenzimidazole, acetate salt

Starting with the compound of Example 2(ii), the title compound was prepared following the procedure of Example 1(ii).

(iv) [5-(4-Cbz-aminoiminomethyl)benzoylamino] benzimidazole-2-amino-N-propanoate, methyl ester Starting with the compound of Example 2(iii), the title compound was prepared following the procedure of Example 1(iii).

(v) [5-(4-Aminoiminomethyl)benzoylamino] benzimidazole-2-amino-N-propanoate, methyl ester, acetate salt Starting with the compound of Example 2(iv), the title compound was prepared following the procedure of Example 1(ii).

(vi) [5-(4-Aminoiminomethyl)benzoylamino] benzimidazole-2-amino-N-propanoic acid, trifluoroacetic acid salt Starting with the compound of Example 2(v), the title compound was prepared following the procedure of Example 1(v). ESMS: m/e 367.2 (M+H)$^+$. Anal. Calcd. for C$_{18}$H$_{18}$N$_6$O$_3$.2C$_2$HF$_3$O$_2$.½H$_2$O: C, 43.79; H, 3.51; N, 13.93. Found: C, 43.61; H, 3.67; N, 14.01.

Example 3

[5-(4-Aminoiminomethyl)phenylaminocarbonyl] benzimidazole-2-amino-N-acetic Acid (i) Methyl 2-amino-N-acetate-5-carboxybenzimidazole Following the procedure of Example 1(i) and starting with 3,4-diaminobenzoic acid in place of 4-nitro-1,2-phenylenediamine, the title compound was prepared.

(ii) 4-(Cbz-aminoiminomethyl)analine

To 4-(aminoiminomethyl)analine dihydrochloride (4.0 g, 19.2 mmol) suspended in tetrahydrofuran (100 mL) and water (20 mL) was added slowly 5N sodium hydroxide (11.6 mL) at 0° C. After 2 minutes, Cbz—Cl was added (3.28 g, 19.2 mmol) dropwise. The reaction was stirred at 0° C. for 1 hour before removing most of the solvent in vacuo. The residue was dissolved in methylene chloride (700 mL), washed with 100 mL of water, dried over sodium sulfate, filtered, and concentrated in vacuo to give the desired product (4.5 g, 87%). This crude product was used without further purification.

(iii) [5-(4-Cbz-aminoiminomethyl)phenylaminocarbonyl] benzimidazole-2-amino-N-acetate, methyl ester The compound of Example 3(i) (0.87 g, 3.49 mmol) was converted to the acid chloride by refluxing with thionyl chloride (7 mL) overnight. The excess thionyl chloride was removed and the residue was mixed with the compound of Example 3(ii) (1.0 g, 3.7 mmol) in methylene chloride (12 mL) and dimethylformamide (5 mL). Triethylamine (1.13 g, 11.2 mmol) was added at 0° C., and then the reaction was stirred at room temperature overnight under argon. The reaction mixture was poured into a flask containing 50 mL of ice to give a brown precipitate (1.76 g, 94%). Flash chromatography (methanol/methylene chloride, 7:93) afforded the desired product.

(iv) [5-(4-Aminoiminomethyl)phenylaminocarbonyl] benzimidazole-2-amino-N-acetate, methyl ester, acetate salt Starting with the compound of Example 3(iii), the title compound was prepared following the procedure of Example 1(ii).

(v) [5-(4-Aminoiminomethyl)phenylaminocarbonyl] benzimidazole-2-amino-N-acetic acid, trifluoroacetic acid salt Starting with the compound of Example 3(iv), the title compound was prepared following the procedure of Example 1(v). ESMS: m/e 353.2 (M+H)$^+$, 351.2 (M−H)$^-$. Anal. Calcd. for C$_{17}$H$_{16}$N$_6$O$_3$.2C$_2$HF$_3$O$_2$: C, 43.46; H, 3.13; N, 14.48. Found: C, 43.76; H, 3.56; N, 14.07.

Example 4

[5-(4-Aminoiminomethyl)benzoylamino] benzimidazole-2-propanoic Acid (i) Methyl 2-propanoate 5-nitrobenzimidazole 4-Nitro 1,2-phenylenediamine (1.54 g, 10 mmol) and mono methyl succinate (2.0 g, 15.1 mmol) were mixed in 4N hydrochloric acid (30 mL) to give a greenish-brown solution. The reaction was stirred at 110° C. for 24 hours, and the solvent was removed in vacuo to give a purple solid. Flash chromatography (methanol/methylene chloride, 5:95) afforded the desired product (0.5 g, 20%).

(ii) Methyl 2-propanoate-5-aminobenzimidazole, acetate salt

Starting with the compound of Example 4(i), the title compound was prepared following the procedure of Example 1(ii).

(iii) [5-(4-Cbz-aminoiminomethyl)benzoylamino] benzimidazole-2-propanoate, methyl ester Starting with the compound of Example 4(ii), the title compound was prepared following the procedure of Example 1(iii).

(iv) [5-(4-Aminoiminomethyl)benzoylamino] benzimidazole-2-propanoate methyl ester, acetate salt Starting with the compound of Example 4(iii), the title compound was prepared following the procedure of Example 1(ii).

(v) [5-(4-Aminoiminomethyl)benzoylamino] benzimidazole-2-propanoic acid, trifluoroacetic acid salt Starting with the compound of Example 4(iv), the title compound was prepared following the procedure of Example 1(v). ESMS: m/e 353.2 (M+H)$^+$, 350.0 (M−H)$^-$. Anal. Calcd. for $C_{18}H_{17}N_5O_3 \cdot 2.33C_2HF_3O_2$: C, 44.11; H, 3.16; N, 11.35. Found: C, 44.51; H, 3.28; N, 10.99.

Example 5

[5-(4-Aminomethyl)benzoylamino]benzimidazole-2-amino-N-acetic Acid (i) [5-(4-Boc-aminomethyl)benzoylamino] benzimidazole-2-amino-N-acetate, methyl ester Starting with the compound of Example 1(ii) (0.7 g, 2.5 mmol) and using 4-(Boc-aminomethyl)benzoic acid (2.5 g, 0.63 mmol), the title compound was prepared following the procedure of Example 1(iii).

(ii) [5-(4-Aminomethyl)benzoylamino]benzimidazole-2-N-amino-acetic acid, trifluoroacetic acid salt Starting with the compound of Example 5(i), the rifle compound was prepared following the procedure of Example 1(v). ESMS: m/e 340.2 (M+H)$^+$, 338.2 (M−H)$^-$. Anal. Calcd. for $C_{17}H_{17}N_5O_3 \cdot 2.5C_2HF_3O_2$: C, 42.31; H, 3.15; N, 11.22. Found: C, 42.09; H, 3.24; N, 11.31.

Example 6

1-N-Benzyl-[5-(4-aminoiminomethyl)benzoylamino] benzimidazole-2-propanoic Acid (i) 1-N-Benzyl-5-nitrobenzimidazole-2-propanoate, methyl ester The compound of Example 4(i) (1.0 g, 4.0 mmol) and sodium hydride (0.11 g, 4.4 mmol) were mixed with tetrahydrofuran (30 mL) and dimethylformamide (5 mL) at room temperature to give a clear brown solution. Benzyl bromide (0.76 g, 4.4 mmol) was added in one portion and then the reaction was stirred overnight at room temperature. The reaction mixture was partitioned in methylene chloride-:water (250:50 mL). The methylene chloride extract was dried over sodium sulfate, filtered, and concentrated in vacuo to give a brownish oil. Flash chromatagraphy (ethyl acetate/hexane, 1:1) separated the two regio-isomers. The higher R$_f$ spot was shown to be the title compound (6(i)(a), 0.68, 50%); whereas, the lower R$_f$ spot was the other isomer, 1-N-Benzyl 6-nitrobenzimidazole-2-propanoate methyl ester (6(i)(b), 0.30 g, 22%).

(ii) 1-N-Benzyl-5-aminobenzimidazole-2-propanoate methyl ester, acetate salt

Starting with the compound of Example 6(i)(a), the title compound was prepared following the procedure of Example 1(ii).

(iii) 1-N-Benzyl-[5-(4-Cbz-aminoiminomethyl) benzoylamino]benzimidazole-2-propanoate, methyl ester Starting with the compound of Example 6(ii), the title compound was prepared following the procedure of Example 1(iii).

(iv) 1-N-Benzyl-[5-(4-aminoiminomethyl)benzoylamino] benzimidazole-2-propanoate, methyl ester, acetate salt Starting with the compound of Example 6(iii), the title compound was prepared following the procedure of Example 1(ii).

(v) 1-N-Benzyl-[5-(4-aminoiminomethyl)benzoylamino] benzimidazole-2-propanoic acid, trifluoroacetic acid salt Starting with the compound of Example 6(iv), the title compound was prepared following the procedure of Example 1(v). ESMS: m/e 442.2 (M+H)$^+$. Anal. Calcd. for $C_{25}H_{23}N_5O_3 \cdot 2.5C_2HF_3O_2 \cdot 2H_2O$: C, 47.25; H, 3.90; N, 9.18. Found: C, 47.59; H, 4.18; N, 8.84.

Example 7

1-N-Benzyl-[6-(4-aminoiminomethyl)benzoylamino] benzimidazole-2-propanoic Acid (i) 1-N-Benzyl-6-aminobenzimidazole-2-propanoate methyl ester, aceate salt Starting with the compound of Example 6(i)(b), the title compound was prepared following the procedure of Example 1(ii).

(ii) 1-N-Benzyl-[6-(4-Cbz-aminoiminomethyl) benzoylamino]benzimidazole-2-propanoate, methyl ester Starting with the compound of Example 7(i), the title compound was prepared following the procedure of Example 1(iii).

(iii) 1-N-Benzyl-[6-(4-aminoiminomethyl) benzoylamino]benzimidazole-2-propanoate, methyl ester, acetate salt Starting with the compound of Example 7(ii), the title compound was prepared following the procedure of Example 1(ii).

(iv) 1-N-Benzyl-[6-(4-aminoiminomethyl)benzoylamino] benzimidazole-2-propanoic acid, trifluoroacetic acid salt Starting with the compound of Example 7(iii), the title compound was prepared following the procedure of Example 1(v). ESMS: m/e 442.2 (M+H)$^+$, 440.0 (M−H)$^-$. Anal. Calcd. for $C_{25}H_{23}N_5O_3 \cdot 2.5C_2HF_3O_2 \cdot 1.5H_2O$: C, 47.82; H, 3.81; N, 9.29. Found: C, 48.14; H, 3.84; N, 9.20.

Example 8

1-N-Phenethyl-[5-(4-aminoiminomethyl) benzoylamino]benzimidazole-2-propanoic Acid (i) 1-N-Phenethyl-5-nitrobenzimidazole-2-propanoate, methyl ester Following the procedure for the preparation of the compounds of Example 6(i)(a) and (b), the two regio-isomers were prepared using phenethyl bromide in place of benzyl bromide. The higher R$_f$ spot was shown to be the title compound; whereas, the lower R$_f$ spot was the other isomer, 1-N-phenethyl 6-nitrobenzimidazole-2-propanoate, methyl ester.

(ii) 1-N-Phenethyl 5-aminobenzimidazole-2-propanoate, methyl ester, acetate salt Starting with the compound of Example 8(i), the title compound was prepared following the procedure of Example 1(ii).

(iii) 1-N-Phenethyl-[5-(4-Cbz-aminoiminomethyl) benzoylamino]benzimidazole-2-propanoate, methyl ester Starting with the compound of Example 8(ii), the title compound was prepared following the procedure of Example 1(iii).

(iv) 1-N-Phenethyl-[5-(4-aminoiminomethyl) benzoylamino]benzimidazole-2-propanoate, methyl ester, acetate salt Starting with the compound of Example 8(iii), the title compound was prepared following the procedure of Example 1(ii).

(v) 1-N-Phenethyl-[5-(4-aminoiminomethyl) benzoylamino]benzimidazole-2-propanoic acid, trifluoroacetic acid salt Starting with the compound of Example 8(iv), the title compound was prepared following the procedure of Example 1(v). ESMS: m/e 456.2 (M+H)$^+$, 454.2 (M–H)$^-$. Anal. Calcd. for $C_{26}H_{25}N_5O_3$·2.5$C_2HF_3O_2$·2$H_2O$: C, 47.94; H, 4.08; N, 9.01. Found: C, 47.58; H, 4.15; N, 8.87.

Example 9

5-[4-Aminoiminomethyl)phenylaminocarbonyl] indole-2-propanoic Acid (i) Benzyl 4-(hydroxyamino)benzoate Hydrazine hydrate (containing 55% hydrazine, 1.5 mL, 26.25 mmol, 1.05 equiv.) was added dropwise over 1 minute to a mixture containing benzyl 4-nitrobenzoate (Brewster, J. H.; Ciotti, C. J., Jr. *J. Am. Chem. Soc.* 1955, 77, 6214; 6.43 g, 25 mmole, 1 equiv.), 5% rhodium on carbon (wet, 625 mg), and tetrahydrofuran (50 ml) at 0° C. under argon. When the addition was complete, the mixture was warmed to room temperature, stirred for 4 hours, and then was filtered through Celite®. Concentration of the filtrate gave crude benzyl 4-(hydroxyamino)benzoate as a yellow oil which was used without further purification. Pure benzyl 4-(hydroxyamino)benzoate, obtained from a separate preparation by silica gel chromatography (30% ethyl acetate/toluene) was used for characterization purposes: TLC(30% ethyl acetate/toluene) $R_f$ 0.52; $^1$H NMR (250 MHz, CDCl$_3$) δ 7.99 (d, J=8.6 Hz, 2 H), 7.26–7.55 (m, 5 H), 6.97 (d, J=8.6 Hz, 2H), 5.33 (s, 2H); IR (CHCl$_3$) 3550, 3315, 1703, 1606, 1273, 1169, 1101, 693 cm$^{-1}$; MS(DC/NH$_3$) 261.2 (M+NH$_4$)$^+$, 245.2 (M+MH$_4$–16)$^+$, 228.1 (M+H–16)$^+$.

(ii) N-[4-(Benzyloxycarbonyl)phenyl]-N-hydroxy-5-(methoxycarbonyl)-3-oxopentanamide A solution of benzyl 4-(hydroxyamino)benzoate (25 mmol, 1 equiv.) and 3-methoxycarbonylpropionyl Meldrum's Acid (Oikawa, Y.; Sugano, K.; Yonemitsu, O. *J. Org. Chem.* 1978, 43, 2087; 7.75 g, 30 mmol, 1.2 equiv.) in dry acetonitrile (125 mL) was heated at reflux under argon. After 45 minutes, the solvent was removed in vacuo and the residue was chromatographed rapidly on silica gel (30% ethyl acetate/toluene). The title compound (7.99 g, 80%, impure) was obtained as a yellow solid. Pure material was used for characterization purposes: TLC (30% ethyl acetate/toluene) $R_f$ 0.39; $^1$H NMR (250 MHz, CDCl$_3$) δ 8.03 (app. d, 2 H), 7.68 (app. d, 2 H), 7.28–7.54 (m, 5 H), 5.63 (s, 1 H), 5.34 (s, 2 H), 3.73 (s, 3 H), 3.06 (d, J=16.7 Hz, 1 H), 2.89 (d, J=16.7 Hz, 1 H), 2.52–2.82 (m, 2 H), 2.25–2.60 (m, 2 H); IR (CHCl$_3$) 3100–3500 (br), 1710, 1357, 1272, 1174, 1108 cm$^{-1}$; MS (DCI/NH$_3$) 417.2 (M+NH$_4$)$^+$, 401.2 (M+NH$_4$–16)+, 400 (M+H)+, 384.1 (M+H–16)$^+$, 287.1, 245, 228.1, 148.1.

(iii) Methyl 5-benzyloxycarbonylindole-2-propanoic acid

A mixture of the compound of Example 1(ii), (7.99 g, 20 mmol, 1 equiv.) and AIBN (65.7 mg, 0.4 mmol, 0.02 equiv.) in p-xylene (Aldrich HPLC grade, 100 mL) was deoxygenated through a single evacuation/argon flush cycle, and the resulting mixture was heated to reflux under argon. A yellow solution was produced which steadily darkened as heating was continued. After 0.5 hour, the reaction was concentrated and the residue was chromatographed on silica gel (twice: run 1: 40% ethyl acetate/hexane; run 2: 2:1 hexane/ethyl acetate. Some crystallization on the column occurred both times). The title compound (1.67 g, 25%; 20% from benzyl 4-nitrobenzoate) was obtained as a yellow solid. TLC (40% ethyl acetate/hexane) $R_f$ 0.51; $^1$H NMR (400MHz, CDCl$_3$) δ 8.82(brs, 1 H), 8.32 (s, 1 H), 7.88 (dd, J=8.6, 1.3 Hz, 1 H), 7.28–7.50 (m, 6 H), 6.31 (s, 1 H), 5.38 (s, 2 H), 3.73 (s, 3 H), 3.07 (t, J=6.5 Hz, 2 H), 2.75 (t, J=6.5 Hz, 2 H); IR (CHCl$_3$) 3200–3500 (br), 1720 (shoulder), 1700, 1303, 1255, 1232 cm$^{-1}$; MS (ESMS) 338.0 (M+H)$^+$.

(iv) Methyl 5-carboxyindole-2-propanoic acid

10% Palladium on carbon (212.8 mg, 0.2 mmol, 0.2 equiv.) was added to a solution of the compound of Example 9(iii) (338.4 mg, 1 mmol, 1 equiv.) in 1:1 ethyl acetate/methanol (30 mL), and the resulting mixture was stirred under hydrogen (40 psi). After 1 hour, the reaction was filtered through Celite® to remove the catalyst, and the filter pad was washed with both ethyl acetate and methanol. Concentration of the filtrate gave the title compound (240.8 mg, 97%) as an off-white solid. TLC (10% MeOH/CHCl$_3$) $R_f$ 0.56; $^1$H NMR (400 MHz, CDCl$_3$ plus DMSO-d$_6$) δ 8.23 (s, 1 H), 7.77 (dd, J=8.5, 1.4 Hz, 1 H), 7.31 (d, J=8.5 Hz, 1 H), 6.27 (s, 1 H), 3.70 (s, 3 H), 3.09 (t, J=7.5 Hz, 2 H), 2.78 (t, J=7.5 Hz, 2 H); MS (ESMS) 248.0 (M+H)$^+$.

(v) [5-[4-Aminoiminomethyl)benzylaminocarbonyl] indole-2-propanoic acid

The title compound is prepared following the procedure of Example 3(iii)–(v), replacing methyl 2-amino-N-acetate-5-carboxybenzimidazole with methyl 5-carboxyindole-2-propanoic acid.

Example 10

5-[(4-Piperidinylacetyl)amino]-1H-benzimidazole-2-butanoic Acid (i) Methyl 2-butanoate 5-nitrobenzimidazole Starting with 4-Nitro 1,2-phenylenediamine (10.0 g, 65.3 mmol) and mono methyl glutarate (15.5 g, 106 mmol), the title compound was prepared following the procedure of Example 4(i).

(ii) Methyl 2-butanoate 5-aminobenzimidazole

Starting with the compound of Example 10(i), the title compound was prepared following the procedure of Example 1(ii).

(iii) 5-[(4-N-Boc-piperidinylacetyl)amino]-1H-benzimidazole-2-butanoate methyl ester Starting with the compound of Example 10(ii) (0.35 g, 1.5 mmol) and using 4-N-Boc-piperidinylacetic acid (0.40 g, 1.65 mmol), the title compound was prepared following the procedure of Example 1(iii).

(iv) 5-[(4-Piperidinylacetyl)amino]-1H-benzimidazole-2-butanoic acid, hydrochloride salt The compound of Example 10(iii) (0.35 g, 0.76 mmol) was dissolved in 10% acetic acid (25 mL) and stirred at 115° C. for 16 hours before adding 1.0N hydrochloric acid (5 mL) directly into the reaction mixture and stirring for additional one hour. The solvent was removed under vacuo to give the crude product (0.33 g, 94%). Purification on reverse phase prep high pressure liquid chromatography (acetonitrile: water, 0.1% trifluoroacetic acid) afforded the trifluoroacetic acid salt. The analytically pure product was converted to hydrochloride salt by dissolving in 1.0N hydrochloric acid and removing the solvent via lyophilization. ESMS: m/e 345.2 (M+H)$^+$, 343.2 (M–H)$^-$. Anal. Calcd. for $C_{18}H_{24}N_4O_3$·3HCl·2$H_2O$: C, 44.14; H, 6.38; N, 11.44. Found: C, 44.51; H, 6.34; N, 11.69.

Example 11

5-[(4-Piperidinylacetylamino]-1H-benzimidazole-2-propanoic Acid (i) 5-[(4-N-Boc-piperidinylacetyl)amino]-1H-benzimidazole-2-propanoate, methyl ester Starting with the compound of Example 4(ii) (0.136 g, 0.62 mmol) and using 4-N-Boc-piperidinylacetic acid (0.166 g, 0.68 mmol), the title compound was prepared following the procedure of Example 1(iii).

(ii) 5-[(4-Piperidinylacetyl)amino]-1H-benzimidazole-2-propanoic acid, hydrochloride salt Starting with the compound of Example 11(i), the title compound was prepared following the procedure of Example 10(iv). ESMS :m/e 331 (M+H)$^+$. Anal. Calcd. for $C_{17}H_{22}N_4O_3 \cdot 2HCl \cdot TFA \cdot 2.75H_2O$: C, 40.04; H, 6.03; N, 10.99. Found: C, 40.13; H, 6.29; N, 10.95.

Example 12

5-[(4-Piperidinylcarbonyl)amino]-1H-benzimidazole-2-butanoic Acid (i) 5-[(4-N-Boc-piperidinylcarbonyl)amino]-1H-benzimidazole-2-butanoate, methyl ester Starting with the compound of Example 10(ii) (0.35 g, 1.5 mmol) and using 4-N-Boc-hexahydroisonicotinic acid (0.38 g, 1.65 mmol), the title compound was prepared following the procedure of Example 1(iii).

(ii) 5-[(4-Piperidinylcarbonyl)amino]-1H-benzimidazole-2-butanoic acid, hydrochloride salt Starting with the compound of Example 12(i), the tide compound was prepared following the procedure of Example 10(iv). ESMS :m/e 331.2 (M+H)$^+$. Anal. Calcd. for $C_{17}H_{22}N_4O_4 \cdot 2HCl \cdot 2H_2O$: C, 46.48; H, 6.42; N, 12.75. Found: C, 46.31; H, 6.11; N, 12.59.

Example 13

5-[[4-(Aminoiminomethyl)benzoyl]amino]-1H-benzimidazole-2-acetic Acid (i) Ethyl 5-nitrobenzimidazole-2-acetate Concentrated nitric acid (5 mL) was added to concentrated sulfonic acid (5 mL) at 0° C., and the solution was cooled thoroughly for an additional 10–15 minutes. Ethyl benzimidazole-2-acetate (Buchi, J.; Zwicky, H.; Aebi, A., *Archiv. Der Pharmazie* 1960, 293, 758; 1.09 g, 5.34 mmol, 1 equiv.) was added portionwise over several minutes The resulting yellow solution was stirred at 0° C. for 20 minutes then was poured carefully onto cracked ice (100 g). The pH was adjusted to 5 with cold 20% sodium carbonate (50–75 mL) and the mixture was extracted with ethyl acetate (3×50 mL). Drying (sodium sulfate), concentration, and silica gel chromatography (3:2 ethyl acetate/toluene) gave ethyl 5-nitrobenzimidazole-2-acetate (1.23 g, 92%) as a yellow solid. TLC (3:2 ethyl acetate/toluene) R$_f$0.44; $^1$H NMR (400 MHz, CDCl$_3$) δ 8.54 (br s, 1H), 8.21 (dd, J=8.9, 2.1 Hz, 1H), 7.58–7.70 (m, 1H), 4.31 (q, J=7.1 Hz, 2 H), 4.14 (s, 2 H), 1.35 (t, J=7.1 Hz, 3 H); IR (chloroform) 3390, 1727, 1523, 1345, 1309 cm$^{-1}$; MS (ESMS) 250.0 (M+H)$^+$.

(ii) Ethyl 5-[[4-(N-Cbz-aminoiminomethyl)benzoyl]amino]-1H-benzimidazole-2-acetate (a) Ethyl 5-aminobenzimidazole-2-acetate A mixture of ethyl 5-nitrobenzimidazole-2-acetate (206 mg, 0.83 mmol, 1 equiv.), 10% palladium on carbon (88 mg, 0.08 mmol, 0.1 equiv.), and absolute ethanol (8 mL) was stirred at room temperature under hydrogen (balloon). After 45 minutes, the reaction was filtered through Celite®, and the filtrate was concentrated to afford crude ethyl 5-aminobenzimidazole-2-acetate. This was used without further purification.

(b) Ethyl 5-[[4-(N-Cbz-aminoiminomethyl)benzoyl]amino]-1H-benzimidazole-2-acetate N-Ethyl-N'(dimethylaminopropyl)carbodiimide ( 191 mg, 1.0 mmol, 2 equiv.) was added all at once to a solution of ethyl 5-aminobenzimidazole-2-acetate (0.83 mmol, 1 equiv.), N-Cbz-(aminoiminomethyl)benzoic acid (272 mg, 0.91 mmol, 1.1 equiv.), 1-hydroxybenzotriazole hydrate (135 mg, 1.0 mmol, 1.2 equiv.), and diisopropylethylamine (0.22 mL, 1.25 mmol, 1.5 equiv.) in dry dimethylformamide (4 mL) at 0° C. under argon. The resulting solution was warmed to room temperature and stirred overnight, then was concentrated on the rotavap. The residue was partitioned between water (20 mL) and ethyl acetate (20 mL), and the layers were separated. The aqueous layer was extracted with ethyl acetate (2×20 mL), and all ethyl acetate layers were combined methanol was added to the combined organic extracts to dissolve suspended solids, and the resulting solution was dried (magnesium sulfate) and concentrated to a yellow solid. Chromatography on silica gel (3:2 acetone/chloroform) gave ethyl 5-[[4-(N-Cbz-aminoiminomethyl)benzoyl]amino]-1H-benzimidazole-2-acetate (316.9 mg, 76% for two steps) as a yellow solid. TLC (3:2 acetone/chloroform) R$_f$0.50; $^1$H NMR (400 MHz, CD$_3$OD) δ 8.08 (s, 1H), 8.04 (d, J=8.5 Hz, 2 H), 7.98 (d, J=8.5 Hz, 2 H), 7.52 (d, J=8.7 Hz, 1H), 7.25–7.50 (m, 6 H), 5.21 (s, 2 H), 4.22 (q, J=7.2 Hz, 2 H), 1.27 (t, J=7.2 Hz, 3 H); The protons α-to the carbethoxy group had exchanged with D from the CD$_3$OD; MS (ESMS) 500.2 (M+H)$^+$, 366.2.

(iii) 5-[[4-(Aminoiminomethyl)benzoyl]amino]-1H-benzimidazole-2-acetic acid

10% Palladium on carbon (68 mg, 0.063 mmol, 0.01 equiv.) was added to a solution of ethyl 5-[[4-(N-Cbz-aminoiminomethyl)benzoyl]amino]-1H-benzimidazole-2-acetate (316.9 mg, 0.63 mmol, 1 equiv.) and trifluoracetic acid (0.049 mL,, 0.63 mmol, 1 equiv.) in absolute ethanol (12 mL), and the mixture was stirred at room temperature under hydrogen (balloon). After 1 hour, the mixture was filtered through Celite® and the filtrate was concentrated to a yellow solid.

This solid was dissolved in absolute ethanol (10 mL) and 1.0N sodium hydroxide (1.9 mL, 1.9 mmol, 3 equiv.), and the resulting yellow solution was stirred at room temperature. A precipitate soon separated. The mixture was stirred for 3 hour, then more 1.0N sodium hydroxide (1.3 mL, 1.26 mmol, 2 equiv.) was added. Stirring at room temperature was continued for another 3 hour, then water (6 mL) was added to afford a clear solution, which was stirred at room temperature overnight. The reaction was concentrated to dryness and the residue was diluted with 1:1 acetonitrile/water (6 mL). The mixture was cooled to 0° C., and trifluoroacetic acid (0.49 mL, 6.3 mmol, 10 equiv.) was added. The resulting yellow solution was concentrated to dryness and the residue was purified by reversed-phase flash chromatography on C-18 silica gel (5% acetonitrile/water/ 0.1% trifluoroacetic acid (300 mL) then 7.5% acetonitrile/water/0.1% trifluoroacetic acid). The product-containing fractions were combined, concentrated on the rotavap to 20 mL, and lyophilized to afford 5-[[4-(aminoiminomethyl)benzoyl]amino]-1H-benzimidazole-2-acetic acid–2 trifluoroacetic acid salt·1.75 water (218.3 mg, 58 as a colorless powder. HPLC (PRP-1 column; 10% CH$_3$CN/water/0.1% trifluoracetic acid) k'=1.10; $^1$H NMR (400 MHz, CD$_3$OD) δ 8.47 (s, 1H), 8.19 (d, J=8.4 Hz, 2 H), 7.96 (d, J=8.4 Hz, 2 H), 7.67–7.77 (m, 2 H); The protons α-to the carbethoxy group had exchanged with D from the CD$_3$OD; MS (ESMS) 338.0 (M+H)$^+$, 294.0 (M+H—CO$_2$)$^+$, 169.4 (M+2 H)$^+$, 146.4; Anal. Calcd for $C_{17}H_{15}N_5O_3 \cdot 2$ CF$_3$CO$_2$H-1.75 water:. C, 42.26; H, 3.46; N, 11.73. Found: C, 42.21; H, 3.14; N, 11.56.

Example 14

Parenteral Dosage Unit Composition

A preparation which contains 20 mg of the compound of Example 4 as a sterile dry powder is prepared as follows: 20 mg of the compound is dissolved in 15 ml of distilled water. The solution is filtered under sterile conditions into a 25 ml multi-dose ampoule and lyophilized. The powder is reconstituted by addition of 20 ml of 5% dextrose in water (D5W) for intravenous or intramuscular injection. The dosage is thereby determined by the injection volume. Subsequent dilution may be made by addition of a metered volume of this dosage unit to another volume of D5W for injection, or a metered dose may be added to another mechanism for dispensing the drug, as in a bottle or bag for IV drip infusion or other injection-infusion system.

Example 15

Oral Dosage Unit Composition

A capsule for oral administration is prepared by mixing and milling 50 mg of the compound of Example 4 with 75 mg of lactose and 5 mg of magnesium stearate. The resulting powder is screened and filled into a hard gelatin capsule.

Example 16

Oral Dosage Unit Composition

A tablet for oral administration is prepared by mixing and granulating 20 mg of sucrose, 150 mg of calcium sulfate dihydrate and 50 mg of the compound of Example 4 with a 10% gelatin solution. The wet granules are screened, dried, mixed with 10 mg starch, 5 mg talc and 3 mg stearic acid; and compressed into a tablet.

The foregoing is illustrative of the making and using of this invention. This invention, however, is not limited to the precise embodiments described herein, but encompasses all modifications within the scope of the claims which follow.

What is claimed is:

1. A compound of the formula (I):

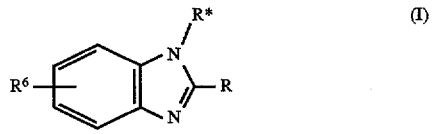

wherein:

R is $R^7$, —$CH_2R^7$, —$CH_2CH_2R^7$, —$CH_2CH_2CH_2R^7$, —$NHCH_2R^7$, or —$NHCH_2CH_2R^7$;

R* is H or —$(CH_2)_{1-2}$phenyl;

$R^6$ is W—$(CR'_2)_q$—Z—$(CR'R^{10})_r$—U—$(CR'_2)_s$—; $(CR'R^{10})_r$—U—$(CR'_2)_s$ is $CH_2NHCO$, $CH(NR'R'')$ CONH, CONH or NHCO;

$R^7$ is —$CO_2H$;

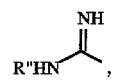

or

R"HNCO—;

each R' independently is H, C1–4alkyl, $C_{3-7}$cycloalkyl-$C_{0-4}$alkyl, or Ar—$C_{0-4}$alkyl;

each R" independently is R' or —C(O)R';

Z is phenyl; and q is 0 to 3;

or a pharmaceutically acceptable salt thereof.

2. A compound which is [5-(4-aminoiminomethyl)-benzoylamino]benzimidazole-2-propanoic acid or a pharmaceutically acceptable salt thereof.

3. A compound which is:

[5-(4-(aminoiminomethyl)benzoylamino]benzimidazole-2-amino-N-acetic acid;

[5-(4-aminoiminomethyl)benzoylamino]benzimidazole-2-amino-N-propanoic acid;

[5-(4-aminomethyl)benzoylamino]benzimidazole-2-amino-N-acetic acid;

[5-(4-aminoiminomethyl)phenylaminocarbonyl] benzimidazole-2-amino-N-acetic acid;

1-N-benzyl-[6-(4-aminoiminomethyl)benzoylamino] benzimidazole-2-propanoic acid;

1-N-benzyl-[5-(4-aminoiminomethylbenzoylamino] benzimidazole-2-propanoic acid; or 1-N-phenethyl-[5-(4-aminoiminomethyl)benzoylamino] benzimidazole-2-propanoic acid;

or a pharmaceutically acceptable salt thereof.

4. A pharmaceutical composition comprising a compound according to claim 1 and a pharmaceutically acceptable carrier.

5. A pharmaceutical composition comprising a compound according to claim 2 and a pharmaceutically acceptable carrier.

6. A pharmaceutical composition comprising a compound according to claim 3 and a pharmaceutically acceptable carrier.

7. A method for effecting inhibition of platelet aggregation to a subject in need thereof which comprises administering a compound according to claim 1.

8. A method according to claim 7 for treating stroke or transient ischemia attacks or myocardial infarction.

* * * * *